(12) United States Patent
Manning et al.

(10) Patent No.: US 10,335,374 B2
(45) Date of Patent: Jul. 2, 2019

(54) TABLET COMPOSITION FOR ANTI-TUBERCULOSIS ANTIBIOTICS

(71) Applicant: University System of Georgia, Valdosta State University, Valdosta, GA (US)

(72) Inventors: Thomas J. Manning, Hahira, GA (US); Sydney E. B. Plummer, Quitman, GA (US); Tess A. Baker, Valdosta, GA (US)

(73) Assignee: University System of Georgia, Valdosta State University, Valdosta, GA (US)

(*) Notice: Subject to any disclaimer, the term of this patent is extended or adjusted under 35 U.S.C. 154(b) by 0 days.

(21) Appl. No.: 14/816,377

(22) Filed: Aug. 3, 2015

(65) Prior Publication Data
US 2016/0038422 A1   Feb. 11, 2016

Related U.S. Application Data

(60) Provisional application No. 62/087,271, filed on Dec. 4, 2014.

(51) Int. Cl.
*A61K 9/20* (2006.01)
*A61K 31/4409* (2006.01)
(Continued)

(52) U.S. Cl.
CPC .......... *A61K 9/2031* (2013.01); *A61K 9/2009* (2013.01); *A61K 9/2018* (2013.01);
(Continued)

(58) Field of Classification Search
None
See application file for complete search history.

(56) References Cited

U.S. PATENT DOCUMENTS 3,639,169 A * 2/1972 Broeg ................. A61K 9/2095
127/29
2009/0192173 A1* 7/2009 Protopopova .......... A61K 31/13
514/255.06

FOREIGN PATENT DOCUMENTS

WO    WO 2012112862 A2 * 8/2012 ................ C07F 1/08
WO    WO-2012112862 A2 * 8/2012 ................ C07F 1/08

OTHER PUBLICATIONS

Manning et al. (The copper (II) ion as a carrier for the antibiotic capreomycin against *Mycobacterium tuberculosis*, Bioorganic & Medicinal Chemistry Letters 24 (2014) 976-982).*

* cited by examiner

*Primary Examiner* — Robert A Wax
*Assistant Examiner* — Melissa S Mercier
(74) *Attorney, Agent, or Firm* — Ballard Spahr LLP

(57) ABSTRACT

Bacterial resistance to antibiotics is increasing worldwide creating a global threat. Tuberculosis (TB), caused by the bacterium *Mycobacterium tuberculosis*, is a bacterial infectious disease that results in over one million deaths annually. The discovery outlined here involves a tablet composition for patient administration and subsequently a new paradigm in drug delivery vehicles in vivo and in vitro and is applied to existing TB antibiotics in order to increase their efficacy. The drug delivery system is a three component complex that is administered with the TB antibiotic or a combination of TB antibiotics. The components are a saccharide or saccharides, a transition metal ion or a combination of metal ions that can bind a nitrogen and/or oxygen atom(s), and a water soluble polymer capable of aggregating and enclosing the other constituents. The three component molecular delivery approach has demonstrated ability to overcome *M. tuberculosis* bacterial resistance to an existing antibiotic.

13 Claims, 11 Drawing Sheets

(51) Int. Cl.
*A61K 38/12* (2006.01)
*A61K 31/496* (2006.01)
*A61K 31/555* (2006.01)
*A61K 31/7036* (2006.01)
*A61K 31/7135* (2006.01)
*A61K 31/77* (2006.01)

(52) U.S. Cl.
CPC ........ *A61K 31/4409* (2013.01); *A61K 31/496* (2013.01); *A61K 31/555* (2013.01); *A61K 31/7036* (2013.01); *A61K 31/7135* (2013.01); *A61K 31/77* (2013.01); *A61K 38/12* (2013.01)

TABLET COMPOSITION FOR ANTI-TUBERCULOSIS ANTIBIOTICS

FIELD OF INVENTION

This disclosure relates to the general field of pharmaceuticals with an emphasis on existing antibiotics. It outlines a process to formulate and construct a tablet including a three component complex consisting of a saccharide, a transition metal cation, and a water soluble polymer, to increase the efficacy of an existing antibiotic or antibiotics used to treat the bacterial disease tuberculosis and resistant strains of tuberculosis.

BACKGROUND

Currently, tuberculosis (TB) ranks as the second leading cause of death from an infectious disease worldwide, after the human immunodeficiency virus (HIV). *Mycobacterium tuberculosis*, the bacterium responsible for causing TB, is unique due to its high content of mycolic acid in its lipid membrane, its slow replication time, and its ability to exploit the mammalian immune system. This bacterium divides slowly, replicating every eighteen to twenty hours, while other species of bacteria can replicate every thirty to sixty minutes. It can resist various disinfectants and can remain inactive for a period of weeks inside a macrophage, a type of cell that is part of the immune system which engulfs foreign harmful material as a defense mechanism. The bacterium has chemical defense systems that prevent it from being neutralized by the macrophage. *M. tuberculosis* transmits from person to person through the air via aerosol droplets containing the bacteria. TB typically infects the lungs, but can also infect other parts of the body. Individuals become contagious when the infection develops from latent to active, and can spread the disease to others by coughing, sneezing, or otherwise dispersing infected droplets through the air. About ninety percent of those infected have asymptomatic, latent TB infections (LTBI), with only a ten percent chance that the latent infection will progress to active TB. However, latent infections that progress to active infections kill more than fifty percent of patients if left untreated. Diagnosis of active TB relies on radiology (chest X-rays), as well as microscopic examination and microbiological culture of sputum or body fluids. Diagnosis of latent tuberculosis relies on the tuberculin skin test (TST) and/or blood tests that vary in complexity, cost and accuracy.

TB treatment requires at least four months of daily therapy with multiple drugs due to the poor efficacy of available antibiotics against different strains of *M. tuberculosis* bacilli. Drug-resistant tuberculosis is caused by *M. tuberculosis* organisms that are resistant to at least one front-line anti-tuberculosis drug. Improper administration and poor adherence by patients when using the two front-line anti-tuberculosis drugs, isoniazid and rifampin, have greatly contributed to the emergence of bacilli that have various levels of resistance to these drugs. This resistance often arises in areas with poor national infrastructure for dispensing and monitoring anti-tuberculosis drugs. Recent World Health Organization (WHO) global surveys have revealed that resistant strains of TB exist in every country examined and has become a significant health problem in areas of Sub-Saharan Africa, Russia, and Central and Southeast Asia. Among drug resistant *M. tuberculosis* isolates, resistance to isoniazid is the most commonly observed form. While the majority of the 2.3 billion people infected with TB worldwide harbor the latent form, a patient that develops an active infection with a drug-resistant TB strain can transmit these strains to other individuals. Increasing incidences of resistant TB infections and costly, inadequate treatment options pose a large barrier for controlling this disease.

Anti-tuberculosis drug resistance is a major public health problem that threatens progress achieved in TB care and control worldwide. Drug resistance arises due to multiple factors, one being improper use of antibiotics when treating drug-resistant tuberculosis such as administration of improper treatment regimens and failure to ensure that patients complete the entire course of treatment. Use of ineffective treatment regimens and difficulty in detecting antibiotic resistance amongst bacterial strains has also exacerbated the evolution of drug resistant *M. tuberculosis* strains. Multidrug resistant tuberculosis (MDR-TB) strains are resistant to the two frontline TB drugs isoniazid and rifampin. Treating drug resistant forms of TB can be complicated, with only a fifty percent cure rate for MDR-TB and further complications caused by toxicity of alternate drugs used. Second-line drugs are a recognized treatment for MDR-TB, but they can cause significant side effects such as ototoxicity. Approximately one out of five MDR-TB patients suffer from permanent hearing loss when given a second-line drug. The cost of the pharmaceutical regimen needed to treat MDR-TB can be, on average, one hundred times greater than active TB treatment regimens, with differing prices based on the economy of the country the case is located in, highlighting a critical component to the embodiment described in this technology. In addition to administration of more costly drugs, the complexity of drug resistant TB treatment should be managed by or in close consultation with an expert in the disease, increasing the cost and care for the patient.

Extensively drug resistant TB (XDR-TB) was first reported in 2006 in Italy. XDR-TB strains are resistant to isoniazid, rifampicin, and the second-line TB drugs fluoroquinolines and at least one of the injectable aminoglycosides. Between 2006 and 2009, there were isolated cases of TB that were not affected by all first and second-line TB drugs. In 2009, over a dozen patients in Iran were resistant to all TB drugs and were considered to have totally drug resistant TB (TDR-TB). Although not as rapidly as MDR-TB, incidence rates of XDR and TDR cases have been increasing worldwide. As different forms of drug resistant TB cases continue to increase, the pursuit for TB control is considerably threatened and cost of second-line drugs impacts their administration.

A person that has developed an active *M. tuberculosis* infection typically undergoes six months of directly observed treatment short-course (DOTS) using a combination of the frontline TB drugs isoniazid, rifampicin, pyrazinamide, and ethambutol. Each of the anti-tuberculosis drugs is more effective at different stages and/or aspects of the disease. For example, isoniazid is utilized in the early stages of treatment therapy; its bactericidal ability reduces the sputum bacterial count because it is primarily active against the bacterium growing aerobically in pulmonary cavities. Pyrazinamide is most active under specific chemical conditions (i.e. acidities), making it functional for inactivating the microbes inside caseous necrotic foci which explains the little benefit of administering pyrazinamide after the second month. Rifampicin inactivates microbes that metabolize slowly, and sterilizes the patient's sputum, as demonstrated in clinical trials.

A limiting factor for effectiveness in TB treatment regimens is the length of treatment which in turn impacts a patient's adherence, affecting progression of infection and can result in resistance to the antibiotics prescribed. The standard regimen for treating latent TB is six months of using only isoniazid, however there is an alternative combination therapy of isoniazid and rifampicin which lasts for a minimum of three months. MDR-TB cases can cause treatment to lengthen up to an additional eighteen months.

Medical and research communities have recognized that new strategies are needed for both drugs and vaccines to combat the global spread of TB and resistant strains of TB. New tuberculosis drugs in development include delaminid, levofloxacin, moxifloxacin, sutezolid, AZD-5847, and SQ109. Delaminid, SQ109, sutezolid and AZD-5847 are at various stages of being evaluated in clinical trials. The vaccine Bacille Calmette-Guerin (BCG) is widely used outside of the U.S. in higher TB burdened countries, but it is also erratic in terms of efficacy and protection lasts less than twenty years. Published reports evaluating BCG indicate its effectiveness ranging from zero to eighty percent. However, the BCG vaccine is beneficial in preventing more severe forms of TB in children such as TB meningitis. Over the past twenty years, developments in vaccines have paralleled developments in genetic based technologies. Currently, there are new tuberculosis vaccines in various levels of development and clinical trials such as MTBVAC (a live-attenuated *M. tuberculosis* based vaccine), MVA85A (a viral vector based vaccine), RUTI (based on fragmented *M. tuberculosis* cells) and Ad5Ag85A (an adenovirus based vaccine). Some TB vaccines have been described in the scientific literature for over a decade but have not been deemed a medical success against various forms of TB.

Bedaquiline, trade name Sirturo, is a diarylquinoline molecule used in the treatment of MDR-TB and has undergone various clinical trials to determine its safety, tolerability, efficacy and rate of resistance acquisition. In December of 2012, the United States Food and Drug Administration approved the new drug to treat adults with pulmonary MDR-TB. When compared to standard regimens, the incorporation of bedaquiline in TB treatment reduced the time to reach sputum culture negativity. The acquisition of drug resistance and the reduction of some adverse effects was lower when using bedaquiline in treatment regimens rather than using it as a single agent. Bedaquiline has been shown to be more effective at curing TB when compared to control groups. More deaths have occurred in bedaquiline recipient groups (11.4%) compared to placebo groups (<3%), but the cause of these deaths was inconclusive and further data must be obtained. The development of bedaquiline is significant because it was the first TB antibiotic approved for the pharmaceutical market in forty years, and it is particularly effective for treating MDR-TB cases.

A common research and development process of antibiotics and other medicines is to test different structural variations of an initial molecule that demonstrates some medicinal efficacy. A prominent example was the initial discovery of penicillin and its bactericidal properties which lead to the development of additional penicillins. Currently there are a number of penicillins that are used including penicillin G, penicillin O, penicillin V, methicillin and amoxicillin that are produced either by microbes or semi-synthesis. Another example of this type of molecular restructuring resulted with the low-cost development of a new class of semisynthetic anti-mycobacterial drugs called spectinamides, which comprises of over one hundred and fifty analogs derived from the antibiotic spectinomycin. Prior to this development, spectinomycin was not utilized as a treatment for TB due to efflux of the drug. However, with structural modification to the drug, the Rv1258c efflux pump can be avoided and binding to the mycobacterial ribosome can increase. The mechanism of action is described as a protein synthesis inhibitor that binds to the 30S ribosome. Spectinamides have shown to have safe pharmacological activity, significantly reduce MIC values, and have activity against MDR-TB and XDR-TB strains. Despite significant work with this group of molecules, none have been introduced to the pharmaceutical market as an anti-tuberculosis drug.

Research and development of new vaccines and new drugs often has extensive time scales and costs involved in the development process. During this process, many drugs are not used to treat patients on a non-trial basis due to medical complications and/or efficacy problems encountered during development.

The pharmaceutical administration method of a drug must not only be effective, but also be able to be utilized by the population in need. The United States Food and Drug Administration defines over one hundred methods of administering the drug to the patient, which includes but is not limited to: auricular (otic), buccal, conjunctival, cutaneous, dental, electro-osmosis, endocervical, endosinusial, endotracheal, enteral, epidural, extra-amniotic, extracorporeal, hemodialysis, infiltration, interstitial, intra-abdominal, intra-amniotic, intra-arterial, intra-articular, intrabiliary, intrabronchial, intrabursal, intracardiac, intracartilaginous, intracaudal, intracavernous, intracavitary, intracerebral, intracisternal, intracorneal, intracoronal, dental, intracoronary, intracorporus, cavernosum, intradermal, intradiscal, intraductal, intraduodenal, intradural, intraepidermal, intraesophageal, intragastric, intragingival, intraileal, intralesional, intraluminal, intralymphatic, intramedullary, intrameningeal, intramuscular, intraocular, intraovarian, intrapericardial, intraperitoneal, intrapleural, intraprostatic, intrapulmonary, intrasinal, intraspinal, intrasynovial, intratendinous, intratesticular, intrathecal, intrathoracic, intratubular, intratumor, intratympanic, intrauterine, intravascular, intravenous, intravenous bolus, intravenous drip, intraventricular, intravesical, intravitreal, iontophoresis, irrigation, laryngeal, nasal, nasogastric, occlusive dressing technique, ophthalmic, oral, oropharyngeal, parenteral, percutaneous, periarticular, peridural, perineural, periodontal, rectal, respiratory (inhalation), retrobulbar, soft tissue, subarachnoid, subconjunctival, subcutaneous, sublingual, submucosal, topical, transdermal, transmucosal, transplacental, transtracheal, transtympanic, ureteral, and vaginal. Many TB patients reside in undeveloped regions and have minimal access to resources available in developed countries which limits the types of pharmaceutical administration methods that can be applied. Currently, many drugs are administered in these conditions using either oral (pill) or intramuscular injection (needle). Intramuscular injected anti-tuberculosis drugs, such as the second-line drugs amikacin and capreomycin, are not ideal forms of treatment due to discomfort for patients and increased care and costs for administration. The embodiment of this work describes a drug administered orally as a pill. To clarify, the form in which a medication is given to a patient (i.e. orally, intramuscular injection) is referred to as drug delivery or administration of the drug. When a molecular level platform such as a micelle, liposome, protein, nanoparticle, aggregate, etc. is used to carry a pharmaceutical agent in vivo or in vitro, it may also be referred to as a drug delivery agent or vehicle but it is at a different stage of administration.

Isoniazid was first described in the scientific literature in 1952. Since then, it has served as a primary antibiotic for reducing the effects of *M. tuberculosis* and has been a standard TB drug for decades. Isoniazid is a prodrug meaning the molecular structure changes upon entering the body. Isoniazid has several mechanisms that contribute to its medicinal activity and side effects including coupling with the $NAD^+/NADP^+$ intermediate species pair, acting to inhibit the unique cell wall lipid synthesis of the bacterium which utilizes mycolic acid, inhibiting nucleic acid synthesis, and decreasing respiration. Isoniazid resistant bacterial strains started being recognized by the medical community in the mid-1950's.

As a group, rifamycins were first identified in 1957 and were later used to treat tuberculosis patients, reducing the duration of treatment from eighteen to nine months. Within this group, rifampin is the most prescribed rifamycin to treat TB. A key structural characteristic of the TB drugs in the rifamycin group is the aromatic structure linked by aliphatic structures giving a relatively nonpolar structure allowing for easy diffusion across the nonpolar *M. tuberculosis* cell membrane, which has a high content of mycolic acid. This anti-tubercular drug group inhibits transcription by complexing a bacterial DNA-dependent RNA polymerase. Development of bacterial resistance to the rifamycin group was first recognized in 1970.

Pyrazinamide was first identified in 1952 and has both bacteriostatic and bactericidal properties. Incorporation of pyrazinamide into TB treatment regimens has reduced treatment length from nine to twelve months to the current six month regimen. Pyrazinamide does not have the same medical efficacy as isoniazid or rifampin, but does have a unique ability to affect dormant populations of *M. tuberculosis* in acidic environments.

Another front-line TB drug that has been used for decades is ethambutol which was first reported to be used against *M. tuberculosis* in 1961. Along with isoniazid, rifampin and pyrazinamide, it is part of the current treatment regimen for TB and works to kill actively replicating bacterium. Three years after its discovery, the first ethambutol resistant bacterial strain was recorded.

Streptomycin, first isolated in 1943, is another front-line antibiotic used to treat patients with TB and belongs to an antimicrobial group called aminoglycosides, which were the first group used to treat TB. Streptomycin may cause side effects including fetal auditory toxicity, neuromuscular paralysis, ototoxcity and nephrotoxicity. Streptomycin bacterial resistance was first recorded in 1950.

These five drugs are defined by the World Health Organization (WHO), a highly influential organization responsible for instilling international treatment recommendations, as Group I TB drugs and compose the standard regimen for treating active TB infections. There are a total of five groups (I, II, III, IV, V) of TB drugs listed by WHO. The Group I TB antibiotics, also called the front-line TB antibiotics, may induce side effects such as allergic reactions, unusual weakness or fatigue, nausea, vomiting, loss of appetite, abdominal pain, neuropathy, seizures, blurred vision, rashes, joint pain, hepatotoxicity, nephrotoxicity, and/or abnormal behavior.

Other TB drugs recognized by WHO include the Group II molecules amikacin, kanamycin, capreomycin, viomycin, and enviomycin; the Group III molecules ciprofloxacin, levofloxacin, and moxifloxacin; the Group IV molecules ethionamide, prothionamide, cycloserine; and the Group V molecules terizidone, rifabutin, clarithromycin, linezolid, thioacetazone, thioridazine, arginine, vitamin D, and bedaquiline. These groupings are used to help determine the type of TB to be treated (i.e. Groups II, III, IV are used to treat different forms of drug resistant TB) as well as effectiveness, cost and side effects. Group V drugs are considered the final choice when other options are not effective. All of these antibiotics contain functional groups (i.e. amines, amides) that can competitively form a strong bond with a cation such as copper (II) and copper (I). Given that all of these molecules have multiple nitrogen and/or oxygen atoms as part of their structures, they qualify as polarity adaptive molecules, which is an important parameter for the embodiment outlined in this disclosure.

Second-line TB drugs that have been evaluated using the delivery system described in this technology are capreomycin and amikacin. Capreomycin, first identified in the early 1960's, is water-soluble and administered intramuscularly via a painful injection. This second-line drug has severe side effects such as ototoxicity, nitrogen retention, electrolyte imbalance, and nephrotoxicity. Capreomycin is more expensive and is only used when front-line drugs are ineffective, in order to treat MDR-TB in combination with other anti-tuberculosis drugs. Amikacin, belonging to the aminoglycoside antibiotic group, is a second-line antibiotic used to treat MDR-TB. Amikacin binds to the 16s rRNA in the 30S small ribosomal subunit, inhibiting protein synthesis. Like capreomycin, amikacin is becoming utilized more often in the treatment of TB due to the increase of MDR-TB cases. Published studies have demonstrated that enclosing the antibiotic in a solid lipid nanoparticle reduced the amount of amikacin needed in TB treatments by half.

Macrophages are a part of the human immune system formed when the body recognizes an infection or when there is an increase in dying or dead cells. Macrophages are a specific type of white blood cell that captures and digests microbes, cancer cells, and other cellular particles that are not protected by a specific protein. Macrophages are large, often measuring more than ten micrometers in diameter and are produced by differentiation of monocytes, groups of white blood cells. When an infection is recognized, the monocytes move from the blood stream to the site of the infection, which is often the lung in *M. tuberculosis* infections. Once in the organ cellular changes occur to the white blood cell, which are unique to the type and location of the infection, as it transforms into a specialized macrophage. These specialized cells can survive for months at a time. Macrophages serve as the host for *M. tuberculosis* to replicate after a process called phagocytosis, or engulfing, the microbe. *M. tuberculosis* then uses the host to remain dormant until progressing into an active infection. The membrane of *M. tuberculosis*, which has high levels of mycolic acid, is presumed to provide protection from a range of internal processes inside the macrophage aimed at destroying the bacterium.

Chemical species can cross a cell membrane in a number of well-known physiological processes such as (1) phagocytosis, a process in which large structures such as bacteria and particles are engulfed (2) pinocystosis, a process in which the fluid phase is taken into the cell by the formation of a small vesicles by the cell membrane (3) macropinocytosis in which large fluid pockets that are greater than one micrometer in size are trapped (4) clathrin-mediated endocytosis which involves the formation of coated pits using cytosolic proteins in the membrane allowing cells to absorb molecules and (5) caveolae-mediated endocytosis in which molecules up to sixty nanometers in diameter are facilitated through the membrane starting with the formation of a membrane dimple. All of these processes are energy dependent and sucrose, which is one component of the drug delivery system described in this embodiment, has been shown to both accelerate and inhibit different endocytosis processes, an idea that supports the basis of this technology.

Applying the principles and advantages of nanotechnology to a drug delivery vehicle can provide the potential to deliver drugs to specific cells using different nanostructures. Drug delivery vehicles focus on maximizing bioavailability at specific locations in the body and for longer periods of time. This can potentially be achieved with molecular targeting by nano-engineered devices. The primary goals of nano-biotechnologies in drug delivery include: increased specificity in drug targeting and delivery, reduction in toxicity while maintaining therapeutic effects, greater safety and biocompatibility, and faster development of safe medicines. Due to the small sizes, nanostructures exhibit unique physicochemical and biological properties (e.g., an enhanced reactive area as well as an ability to cross cell and tissue barriers) making them a favorable material for biomedical applications and a growing area of novel research.

Other drug delivery vehicle approaches including micelles, liposomes, dendrimers and proteins have been involved in a large number of preliminary studies, but few candidates have been advanced through clinical trials for antibiotics. Many of these compounds have no direct medicinal effect or activity but serve to increase residence time in blood, thereby increasing exposure of the pharmaceutical agent to the disease. For example, poly-lactide-co-glycolide (PLG) nanoparticles have been used as drug delivery agents for rifampin, isoniazid, pyrazinamide and ethambutol against *M. tuberculosis* and have been shown to produce increased bioavailability and improved pharmacodynamics activity. The Alginate nanoparticle, a biodegradable composite, has been used to deliver rifampin, isoniazid, pyrazinamide and ethambutol to treat patients with *M. tuberculosis* infections and has demonstrated to have a high drug payload, improved pharmacokinetic activity and high therapeutic efficacy in clinical studies. A liposome system composed of hydrogenated soy phosphatidylcholine, cholesterol, and distearoylphosphatidylglycerol (DSPG) have been used to deliver the second-line TB drug amikacin against gram-negative bacteria and has shown to have prolonged drug exposure. In another published report, a lipid nanoparticle composed of stearic acid has been used to deliver rifampicin, isoniazid, and pyrazinamide to treat patients with *M. tuberculosis* and has demonstrated increased residence time, increased drug bioavailability, and decreased administration frequency.

An example of a dendrimer used to deliver an antibiotic is polyamidoamine (PAMAM) dendrimers which have been used to deliver the antibiotics nadifloxacin and prulifloxacin against various types of bacterial infections and has demonstrated increased water solubility, an important parameter due to the aqueous nature of blood. Another example of a nano-dendrimer system is the glycosylated polyacrylate nanoparticle which has been utilized to deliver the Beta-lactam ciprofloxacin against the bacterium *Staphylococcus aureus* and *Bacillus anthracis*, and demonstrated improved bioavailability and higher therapeutic efficacy. All of the drug delivery systems mentioned thus far do not provide an increase in the medicinal efficacy of the drug but are chemically inert and serve to make the drug more available at the diseased or infected site. The new technology described in this disclosure is a molecular method of drug delivery composed of three components bonded together with one or more anti-tuberculosis antibiotics and enclosed with a polymer to increase efficacy of the drug.

Liposomes, which are composite structures made of phospholipids that may contain small amounts of other molecules, are one of the most common molecular based vehicles used for targeted drug delivery. Liposomes can vary in size from nanometers to tens of micrometers. Unilamellar liposomes are smaller in size, with various targeting ligands attached to their surface, allowing for surface-attachment and accumulation in diseased areas. One issue in using liposomes is the immediate uptake and clearance by certain physiological systems when used in vivo and low stability when used in vitro. To overcome this problem, different forms of polyethylene glycol (PEG) are added to liposomes which can increase circulation time up to five fold. Another type of drug delivery vehicle used is polymeric micelles. Polymeric micelles are nanoscopic core/shell structures formed by amphiphilic block copolymers.

To understand the relevance of this invention and subsequent disclosure, it is important to review previous revealed intellectual property disclosures to recognize developments in the field. There are several drug delivery designs at the molecular level such as liposomes, polymeric micelles, lipoproteins, dendrimers, nanoparticles, and albumin. Typical parameters for a molecular level drug delivery vehicle include biodegradability, no toxicity, biocompatibility, and inability to be detected by immune mechanisms. Most of the well-recognized delivery systems are significantly larger and heavier than the medicinal agent they are transporting. Two unique aspects to the formulation disclosed in this application are (a) two of the delivery components used (i.e. copper(II), sucrose) are similar in size to the active ingredients (TB drugs) they help deliver and (b) the delivery components can impact biochemical cycles by serving as nutrients to improve efficacy of the drug and each can be toxic in another cellular biochemical cycle. Using examples below, novel developments in drug delivery involves platforms that are inert from a pharmaceutical perspective.

U.S. Pat. No. 8,394,839 B2, entitled "Rationally improved isoniazid and ethionamide derivatives and activity through selective isotopic substitutions" describes the use of exchanging the carbon-12 isotope, which has a natural abundance of 98.9%, with carbon-13 isotopes, which has a natural abundance of 1.1%. This disclosure revealed that the anti-tuberculosis drugs isoniazid and ethionamide could have improved medical efficacy against mycobacterial diseases using this isotope based technology.

U.S. Pat. No. 8,449,916 B1 entitled "Antimicrobial compositions and methods" describes treating and killing microbial infections in animals. This technology focuses on the use of polyanhydride microparticles, defined by diameters of at least one micrometer, and nanoparticles, defined by diameters between one and nine hundred and ninety nine nanometers. The particles defined contain a microbial agent that will slowly dissolve and release the pharmaceutical agent to treat the infection.

Patent EP 18774226 B1 (from WO2006117240A2) describes a method of inhibiting the activation of latent or active *M. tuberculosis* using a nucleic acid encoding an Mtb72f fusion protein. The invention also claims to shorten the drug regimen administration time scale for TB. The patient, which is described as a mammal, must have been previously immunized by the BCG vaccine.

U.S. Pat. No. 8,597,616 B2 entitled "Dry Powder drug delivery formulations, methods of use, and devices therefore" describes a new technology related to the use of a dry powder to deliver a pharmaceutical formulation for pulmonary applications. While the invention outlines the use of the delivery methods for patients with TB, it may also deliver therapeutic agents to treat exposure to nerve agents and toxic gas.

WO 2011016043 A2 also published as U.S. Pat. No. 8,951,563 entitled "Antibiotic drug delivery and potentiation" describes the use of a cochleate-based delivery system. The cochleate system, which can have a positive charge as great as +10, is composed of residues of amino acids and an amino-fatty acid moiety.

U.S. Pat. No. 6,455,073 B1 entitled "Covalent microparticle-drug conjugates for biological targeting" describes a novel method to deliver antiviral, antimicrobial and antibiotic drugs to cells with phagocytic capabilities. The active ingredients in the microparticles include isoniazid, rifampin, capreomycin, ethionamide, amikacin, and cycloserine. The preparation involves a number of serivazation and synthetic routes such as the synthesis of a carbamate derivatized polymer coating, as well as several processes that involve the release of the drug such as urease catalyzed release from polymer-coated microparticles.

U.S. Pat. No. 8,110,181 B2 describes a method that uses an aerosol generator to deliver interferons. Alpha, beta, and gamma interferons are one active component of the aerosol. The aerosol delivery of the interferons is for the treatment of pulmonary diseases. The interferon is combined with some antibiotic agents and delivered in doses between ten and one thousand milligrams.

U.S. Pat. No. 8,697,653 B2 entitled "Microparticle formulation for pulmonary drug delivery of anti-infective molecule for treatment of infectious diseases" describes an inhalable microparticle coupled with a biodegradable lipid that can be used as a delivery system for the treatment of pulmonary TB, MDR-TB, Methicillin-resistant *Staphylococcus aureus* (MRSA) pneumonias and Methicillin-sensitive *Staphylococcus aureus* (MSSA) pneumonias by delivering the recommended amount of the pharmaceutical agent to the patient.

There are currently no drug delivery agents or drug boosters improving efficacy on a molecular level that are used to deliver TB antibiotics that have been approved by the United States Food and Drug Administration or are approved by multinational agencies that recommend TB treatment regimens such as the World Health Organization.

This invention focuses on the composition of a tablet with a drug delivery platform that, when administered in vivo or in vitro, consists of an existing antibiotic, a saccharide, a transition metal cation and a polymer to increase the efficacy of the drug by impacting physiological processes. Additional species are included in the tablet to help with other facets of tablet composition, rigidity, dissolution and ingestion. When developing a drug delivery agent, the toxicity, pharmacodynamics, pharmacokinetics and medical efficacy of each component should be considered.

Polyethylene glycol (PEG-3350) has approval for use in the pharmaceutical industry by the Food and Drug Administration. Brand names that PEG are sold under include clenz-lyte, co-lav, colovage, colyte, colyte with flavor packs, e-z-em prep lyte, glycolax, glycoprep, go-evac, golytely, halflytely, lax-lyte with flavor packs, miralax, mircera, moviprep, nulytely, nulytely-flavored, PEG 3350 and electrolytes, PEG-lyte, suclear, and trilyte. The general mechanism of action for PEG is the osmotic effect causing water to be retained in the digestive tract and results with liquefaction of feces. The pharmacodynamics induce a liquid stool which cleans the lower gastrointestinal tract within four to six hours. Pharmacokinetic data for pure PEG indicates that as the polymer gets larger, it absorbs through the intestinal tract at a lower rate.

As described in the peer reviewed scientific literature, maximum PEG-3350 plasma concentrations occur at approximately three hours after a single dose, and a non-detectable level is reached eighteen hours after administration. Less than one percent of the polymer is excreted in urine while over ninety percent is excreted in fecal matter. In this embodiment, the role of PEG is to form an aggregate and provide a carrier through the gastrointestinal tract, trapping the transition metal cation-saccharide-antibiotic complex and allowing it to cross the membrane to the serum. PEG can be administered by intravenous, oral, rectal, and topical routes and is found in household products such as toothpaste, shampoo, moisturizers, and some foods. It has been demonstrated that PEG not only forms aggregates in a physiological environment, but also that macrophages will ingest these foreign and loosely formed nanoparticles because they are not recognized. By itself, PEG-3350 has no useful pharmaceutical activity against *M. tuberculosis*.

The process of PEGylation has dramatically increased the use of PEG in the drug delivery field. PEGylation involves attaching molecules of various sizes and uses to the polymer, potentially providing a number of improvements or advantages including increased drug stability, increased residence time in the body or serum, increased drug solubility in water or serum, protection from hydrogen bonding to unwanted species (applied Lipinski's Rule of Five), protection from acid catalyzed reactions, and reduced degradation due to enzymes. Preliminary ADME (absorption, distribution, metabolism, and excretion) studies for PEGylated compounds indicated the functionalized species containing PEG have improved values compared to the pure compounds. There are a number of PEGylated compounds available in the pharmaceutical market now including: Naloxegol (Movantik), Peginesatide (Omontys), Pegloticase (Krystexxa), Certolizumab pegol (Cimzia), Methoxy polyethylene glycol-epoetin beta (Mircera), Pegaptanib (Macugen), Pegfilgrastim (Neulasta), Pegvisomant (Somavert), Peginterferon alfa-2a (Pegasys), Doxorubicin HCl liposome (Doxil/Caelyx), Peginterferon alfa (Peglntron), Pegaspargase (Oncaspar), and Pegademase bovine (Adagen).

The disaccharide sucrose is utilized as an inert ingredient in syrups, gums, chewable tablets, and lozenges. Excess sucrose consumption can be correlated with dental cavities, diabetes and weight gain. Sucrose is found in a number of available drugs including; Acetaminophen and Hydrocodone Bitartrate, Adipex, Amphetamine and Dextroamphetamine Extended Release, Cymbalta, Dexamethasone, Levothyroxine Sodium, Lortab, Methylphenidate Hydrochloride, Metoprolol Succinate, Norco, Omeprazole, Phendimetrazine Tartrate and Phentermine Hydrochloride. A saccharide such as sucrose incorporated into the drug delivery system outlined in this embodiment serves as one of the components acting as a nutrient increasing uptake of the drug attached and inducing one or more physiological processes within the target to increase efficacy of the drug.

Another consideration in this embodiment is the incorporation of a transition metal cation such as copper, a copper salt, zinc, a zinc salt, iron, an iron salt, nickel or a nickel salt as a carrier. All of these metals are essential nutrients in the body at low levels but can cause toxicity at higher concentrations. The toxicity level can vary depending on whether the cation is administered as a free ion (i.e. copper (II)(aq), nickel(II)(aq)) or bound to a species such as a protein or a small molecule. For example, copper gluconate or copper citrate are two examples of copper complexes used for treating copper deficiency, a rare disorder that occurs from a lack of zinc in diets, intestinal bypass surgery, and Menkes disease. Copper is an important nutrient that is found in a number of enzymes (2-furoyl-CoA dehydrogenase, Amine oxidase, Bilirubin oxidase, Catechol oxidase, etc.) and proteins (cytochrome c oxidase, hemocyanin, tyrosinase, amicyanin, plastocyanin and pseudoazurin). A healthy adult has approximately two parts per million copper in their body, but over ninety-nine percent of this copper is utilized by and incorporated in enzymes and proteins. Adding a transition metal ion such as copper to the drug delivery system outlined in this embodiment serves as one of the components acting as a nutrient increasing uptake of the drug attached, inducing one or more physiological processes within the target to increase efficacy of the drug, increasing the structural stability of the drug, and/or serving independently as a biocide.

The quantities of each component of the drug delivery system including the existing anti-tuberculosis drug that may be used are given as an example, but are not to be construed to be in any way limiting for the present invention. Using the front-line anti-tuberculosis drug isoniazid as an example, the quantities of the additional components and antibiotic of the drug delivery system are given as a 1:1:1:1 ratio and are as follows: 10 milligrams of isoniazid, 24.96 milligrams of sucrose, 12.408 milligrams of copper (II) chloride dihydrate, and 244.52 milligrams of PEG-3350. Additional examples of quantities for this technology are given later in this disclosure.

SUMMARY OF INVENTION

This discovery is focused on a tablet composition with three components including a saccharide or mixture of saccharides, a water soluble polymer or mixture of water soluble polymers and a transition metal cation or a mixture of transition metal cations, utilized to increase the efficacy of existing tuberculosis (TB) antibiotics. These additional components serve to bind, aggregate and transport the antibiotic or antibiotic mixture to the infected site. To fully understand this tablet composition, results for one (i.e. copper or PEG-3350) and two component systems (copper, PEG-3350) at both a molecular level using analytical techniques such as Nuclear Magnetic Resonance (NMR), Liquid Chromatography-Mass Spectrometry (LCMS), Fourier Transform-Ion Cyclotron Resonance (FT-ICR), Matrix Assisted Laser Desorption Ionization-Mass Spectrometry (MALDI-TOF-MS), and cell line studies testing their efficacy against *Mycobacterium tuberculosis* are discussed in this section. The three component system is defined in detail in the Detailed Description section.

Polyethylene glycol (PEG) is a water soluble polymer available in different molar masses. The polymer is widely used for medicinal purposes and has been complexed with various pharmaceutical agents to increase residence time of drugs in the host organism resulting in an increased amount of the drug being delivered to its target. PEG structures can impact a biological system in a number of ways including precipitating proteins, blocking osmosis at a cell membrane, and forming micelles by aggregating with naturally occurring lipids. PEG has been used as a multiple polymer compound for core shell nanoparticles which have shown to increase bioavailability of isoniazid by twenty-eight fold. PEG derivatives of isoniazid have shown to have lower cytotoxicity and increased residence time at infection sites compared to isoniazid alone. Increasing molecular weights of PEG complexed with isoniazid has resulted in higher residence time in the bloodstream as well. In this work, PEG is utilized to enclose the TB antibiotic or mixture of antibiotics and the additional components, copper and sucrose, in order to increase residence time and remain unrecognizable by the human immune system.

The biocide and antimycobacterial activity of the copper (II) ion has been outlined in a number of published studies. Isoniazid complexes with copper(II) by binding with oxygen and/or nitrogen atoms. The addition of copper(II) to isoniazid increases activity against mycobacteria especially under high iron conditions (8 micrograms/milliliter). The role of copper ions is recognized in the interaction between macrophages and some intracellular pathogens. While copper is an essential nutrient for *M. tuberculosis*, an overload within the organism is lethal. Copper serves a critical role in controlling TB as demonstrated in scientific literature where *M. tuberculosis* isolates that did not have the protein Rv1698 accumulated significant levels of copper, and therefore were more likely to succumb to copper toxicity. *M. tuberculosis* is more susceptible to copper biocide properties than other bacteria that are found in the phagosomes of macrophages but cellular processes serve to protect the microbe from the biocide. In this work, copper is utilized, directly and indirectly, to increase uptake of the drug attached to it and affect one or more physiological processes within the target.

A published report studied the use of mannitol, a carbohydrate alcohol, and sucrose as carriers for the front-line antibiotics isoniazid and rifampin. Mannitol was used as a carrier for the first-line TB drugs using a powder inhaler. The scientific literature provides no insight into utilizing monosaccharides or disaccharides and transition metal ions such as copper ions complexed to a known antibiotic, specifically a TB drug, aggregated by a water soluble polymer such as PEG functioning as a drug delivery platform.

The first antibiotic complex investigated with one and two component systems consisted of the second-line TB drug capreomycin which was bound to the copper(II) cation and the aggregate forming water soluble unbranched polymer PEG-3350. Capreomycin was tested with one (copper ion or PEG) and two component (copper ion and PEG) systems, and the minimum inhibition concentrations (MIC) values were determined. MIC values are defined as the lowest concentration of an antimicrobial (i.e. antifungal, antibiotic or bacteriostatic) drug that will inhibit the visible growth of a microorganism after incubation and is a common unit used to describe the level of efficacy of an antibiotic against a bacterium. The MIC values against active TB were measured to be capreomycin (3.13 micromolar), copper(II) chloride (0.39 micromolar), copper-PEG (50.0 micromolar), copper-capreomycin (3.13 micromolar), capreomycin-PEG (1.56 micromolar), and copper-PEG-capreomycin (0.2 micromolar). PEG exhibited no measureable pharmaceutical activity against the bacterium.

Additional studies were conducted involving the copper-capreomycin complex which lowered or improved MIC values two hundred and fifty (250) times against drug resistant strains of *M. tuberculosis*. This set of data demonstrated that the performance of a known anti-tuberculosis antibiotic had an improved efficacy with this delivery system which warranted further studies and proposal of new structures.

Molecules can shift polarity and their dipole moment based on their specific geometry and ability to bind other species such as cations. Polarity adaptive molecules occur when a cation (i.e. copper(II), iron(II), zinc(II)) binds a molecule that contains multiple electronegative atoms such as nitrogen, oxygen, fluorine and/or sulfur. The cation does not form a strong bond at one site on the molecule, but it moves around the chemical structure, between electronegative elements forming and breaking a series of ion-dipole and/or weak covalent bonds. This atomic level movement can be measured using the analytical technique Nuclear Magnetic Resonance (NMR). Shifts in spectral features including line position (in ppm) and the line profile shape for the molecule provides information for this interaction. Proton ($^1$H) and carbon ($^{13}$C) NMR has been used to study the polarity adaptive molecule effect in some anti-tuberculosis drug structures outlined in this disclosure. Figure one provides a sample-set of two spectra that provide evidence for the copper ion binding to capreomycin, which resulted in capreomycin being described as a polarity adaptive molecule. In terms of delivering a drug to a specific location, a cation being in one position on a molecule results in the metal-molecule complex having a dipole moment that qualifies as a polar complex that has some solubility in water. When the cation moves to another location on the molecule, the dipole moment decreases giving the complex a more nonpolar nature which can allow it to pass through a nonpolar lipid cell membrane.

In a series of one and two component complex studies with amikacin, the $IC_{50}$, $IC_{90}$ and MIC values were measured against active and resistant strains of M. tuberculosis by the United States National Institutes of Health—National Institute of Allergies and Infectious Diseases. $IC_{50}$ refers the amount of drug needed to inhibit fifty percent of the bacterial growth and $IC_{90}$ refers to the amount of drug needed to inhibit ninety percent of the bacterial growth. Pure amikacin had $IC_{50}$, $IC_{90}$ and MIC values against *M. tuberculosis* of 0.216 micromolar, 0.328 micromolar and 0.390 micromolar, respectfully, in the cell line studies conducted. The one component copper-amikacin complex had improved MIC values of <0.20 micromolar, <0.20 micromolar, and 0.196 micromolar, each indicating a higher level of efficacy compared to the pure antibiotic. The copper-PEG aggregate produced MIC values of 13.328 micromolar, 17.106 micromolar and 25 micromolar, all at least ten times higher than the MIC values produced with pure amikacin. The activity measured for this non-antibiotic complex is likely due to the biocide activity of the copper ion. The amikacin-PEG complex produced $IC_{50}$, $IC_{90}$ and MIC values of <0.20 micromolar, <0.20 micromolar and 0.196 micromolar, all less than the values of the pure antibiotic. The two component complex copper-amikacin, highlighted by copper-nitrogen bonds trapped in a PEG aggregate, resulted in $IC_{50}$, $IC_{90}$ and MIC values of <0.20 micromolar, <0.20 micromolar, and 0.196 micromolar. This work with one and two components complexes tested against drug susceptible *M. tuberculosis* led to a second set of experiments with amikacin and resistant strains of *M. tuberculosis.*

The MIC values provided below were measured against (a) the H37Rv strain in (micromolar) (b) the isoniazid-resistant strain (c) the rifampin-resistant strain (micromolar) (d) the ofloxacin-resistant strain (micromolar), respectfully listed below. The second-line TB drug amikacin gave MIC values of 0.256 micromolar, 2.05 micromolar, 0.256 micromolar, and 0.256 micromolar, respectfully. Testing the copper-amikacin complex resulted in values of 0.231 micromolar, 1.85 micromolar, 0.231 micromolar and 0.231 micromolar against the active and resistant strains of TB which are slightly lower MIC values than the antibiotic alone. The copper-PEG aggregate had MIC values of 1.37 micromolar, 10.9, micromolar, 2.74 micromolar and 2.74 micromolar. Although these values are roughly an order of magnitude greater than the antibiotic complexes, the activity observed can be attributed to the copper cation. The amikacin-PEG aggregate had MIC values of 0.0381 micromolar, 0.305 micromolar, 0.152 micromolar and 0.152 micromolar, respectively. The MIC value for the H37Rv strain is almost an order of magnitude lower than the MIC values for pure amikacin. The two component complex consisting of copper-PEG-amikacin had MIC values of 0.157 micromolar, 0.3001 micromolar, 0.3001 micromolar, and 0.3001 micromolar, respectively.

In addition to the cell line studies, analytical chemistry studies were pursued to ensure that the copper (II) ion was bonding to the antibiotics. Techniques such as NMR, LC-MS, MALDI-TOF-MS and FT-ICR were used to provide detailed information about the structure and the interaction of the different components. For example, figure two provides NMR spectra of the copper-amikacin complex. The copper ion is paramagnetic and causes shifts and broadening in the proton NMR spectra allowing for the determination of the location of the copper ion binding to the antibiotic. This representative data is used to demonstrate that the copper-amikacin complex is a polarity adaptive molecule. Another representative experiment is shown in figure three which provides a MALDI-TOF-MS spectrum of the copper-amikacin complex. This clearly provides experimental evidence for the formation of the cation-antibiotic complex and supports the NMR data.

Another set of studies conducted as part of this discovery process involved one and two component complexes with the front-line TB drug rifampicin. All of the experimentally determined in vivo measurements cited in this disclosure were measured by the National Institutes of Health—National Institute of Allergies and Infectious Diseases. Pure rifampicin was measured against the H37Rv strain of *M. tuberculosis* and the MIC value was determined to be 0.006 micromolar. The MIC value for pure copper (II) chloride dihydrate measured against the H37Rv strain of *M. tuberculosis* was determined to be 105.7 micromolar. The MIC value for pure PEG measured against the H37Rv strain of *M. tuberculosis* was determined to be >100 micromolar, meaning it had no efficacy of interest. The MIC value for the copper-rifampicin complex measured against the H37Rv strain of *M. tuberculosis* was determined to be 0.03 micromolar. The MIC value for the copper-PEG complex measured against the H37Rv strain of *M. tuberculosis* was determined to be >100 micromolar. The MIC value for the rifampicin-PEG complex measured against the H37Rv strain of *M. tuberculosis* was determined to be 0.003 micromolar, roughly half the inhibiting concentration of the pure compound. The MIC value for the copper-rifampicin-PEG complex measured against the H37Rv strain of *M. tuberculosis* was determined to be 0.006 micromolar. These values indicate a slight improvement in MIC values for the rifampicin-PEG complex while the other complexes are similar to or slightly lower than pure rifampicin. This set of data demonstrates that none of the additional components significantly altered or interfered with rifampicin.

In a second set of experiments the MIC, $IC_{50}$ and $IC_{90}$ values (micromolar) were measured in aerobic conditions for rifampicin and three different rifampicin complexes. The rifampicin values were 0.004 micromolar, 0.003 micromolar and 0.003 micromolar, while the PEG-rifampicin values were 0.004 micromolar, 0.004 micromolar and 0.007 micromolar, the copper-rifampicin values were 0.009 micromolar, 0.005 micromolar, and 0.01 micromolar, while the copper-rifampicin-PEG complex values were 0.008 micromolar, 0.004 micromolar and 0.009 micromolar. While these values are relatively similar, they do indicate that the two components, copper and PEG did not significantly alter or interfere with rifampicin.

In a third set of experiments the MIC, $IC_{50}$ and $IC_{90}$ values were measured in low oxygen conditions (Low Oxygen Recovery Assay). For pure rifampicin the values were 0.0003 micromolar, 0.0007 micromolar and 0.0022 micromolar. For the copper-rifampicin complex the values were 0.0003 micromolar, 0.0010 micromolar and 0.0031 micromolar. The rifampicin-PEG compound produced the values of 0.0003 micromolar, 0.0007 micromolar and 0.0021 micromolar. The copper-PEG-rifampicin complex produced the values of 0.0004 micromolar, 0.0008 micromolar, and 0.0018 micromolar, respectively. A key point in evaluating the MIC value results found in a low oxygen environment, which represents the internal conditions of a macrophage, is that all of the antibiotic complexes tested maintained activity.

The next set of data used to evaluate the one and two component rifampicin complexes evaluated the minimum bactericidal concentration (MBC) values for four samples. Antibacterial agents are considered bactericidal if the MBC values are, at most, four times the MIC values. While none of the components tested were below the standard value of four, the data does suggest that both the copper-PEG-rifampicin and PEG-rifampicin complexes have stronger antibacterial properties than pure rifampicin. The MBC and the MBC/MIC values for rifampicin were 0.06 micromolar and 15; the values for the copper-rifampicin complex were 0.15 micromolar and 16.6; the values for the rifampicin-PEG values were 0.03 micromolar and 7.5; and the copper-PEG-rifampicin complex produced values of 0.06 micromolar and 7.5, respectively.

The next set of data examined the reduction of colony forming units (CFUs) at different concentrations to determine intracellular activity of each sample. The CFU units for rifampicin and copper-PEG-rifampicin were measured at 0.006 and 0.06 micromolar, while copper-rifampicin and PEG-rifampicin were measured at half those concentrations (0.003 micromolar, 0.03 micromolar). While the values are statistically similar in terms of reducing CFU's, the two complexes, rifampicin-PEG and copper-rifampicin show a linear decrease with concentration while pure rifampicin is not linear. The values are reported as the log reduction of CFUs, a unit-less number. Specifically, rifampicin (0.006 micromolar, 0.06 micromolar) had values of 0.9 and 2.5; the copper-rifampicin (0.003 micromolar, 0.03 micromolar) complex had values of 1.1 and 2.1; the rifampicin-PEG complex (0.003 micromolar, 0.03 micromolar) had values of 0.9 and 1.9; the copper-PEG-rifampicin complex (0.006 micromolar, 0.06 micromolar) had values of not available (N/A) and 1.8.

The next set of experiments focuses on cell line studies for the activity of the four rifampicin complexes against isoniazid, rifampicin, and fluoroquinolone resistant strains of *M. tuberculosis*. The first strain used was INH-R1 (isoniazid resistant), which was derived from H37Rv and is a katG mutant (Y155*=truncation). Mutations in the *M. tuberculosis* genome causing resistance to isoniazid are most commonly found in the katG gene, disrupting activation of the prodrug. The MIC values for rifampicin (0.020 micromolar), copper-rifampicin (0.014 micromolar), rifampicin-PEG (0.020 micromolar) and copper-PEG-rifampicin (0.030 micromolar) are important because none of the complexes loses significant efficacy against the resistant strains. The second strain was INH-R2 (isoniazid resistant), which was derived from strain ATCC35822. The values for rifampicin (0.0075 micromolar), copper-rifampicin (0.0078 micromolar), rifampicin-PEG (0.00740 micromolar) and copper-PEG-rifampicin (0.00830 micromolar) are important because none of the complexes lose significant efficacy against the resistant strains. The third strain was RIF-R1 (rifampicin resistant) which was derived from H37Rv and is an rpoB mutant (S522L), which causes rifampin to no longer be able to bind to RNA polymerase causing interference with transcription. The values for rifampicin (12.4 micromolar), copper-rifampicin (12.6 micromolar), rifampicin-PEG (14.8 micromolar) and copper-PEG-rifampicin (13.7 micromolar) were measured. The fourth strain was RIF-R2 (rifampicin resistant) from strain ATCC35828. The values for rifampicin (>200 micromolar), copper-rifampicin (>200 micromolar), rifampicin-PEG (>100 micromolar) and copper-PEG-rifampicin (>100 micromolar) indicate that pure rifampicin or any of the one (PEG or copper ion) or two component systems (PEG and copper ion) have no medicinal efficacy against this resistant strain. The fifth strain was FQ-R1 (fluoroquinolone resistant), a fluoroquinolone-resistant strain derived from H37Rv and has an unidentified mutation. The values for rifampicin (0.017 micromolar), copper-rifampicin (0.025 micromolar), rifampicin-PEG (0.018 micromolar) and copper-PEG-rifampicin (0.015 micromolar) resulted. From these results it can be concluded that in the relatively uncomplicated in vitro environment, the copper(II) ion and the PEG polymer or the combination of the two binding and forming an aggregate with the rifampicin compound does not interfere with its delivery or efficacy.

In addition to the cell line studies, a number of analytical experiments using FT-ICR, NMR, MALDI-TOF-MS and LC-MS were conducted to further understand the structure of the different complexes. Figure four provides a $^1H$ NMR spectrum of the pure rifampicin molecular structure, which contains complicated spectral features with numerous peaks. In addition, the impact that the paramagnetic copper salt has on the proton NMR spectra of rifampicin is illustrated, clearly demonstrating that many spectral features disappear which is a common effect observed when a paramagnetic species binds an organic molecule. Figure five provides insights to four spectra acquired from a FT-ICR located at the National High Field Magnet Lab (Tallahassee, Fla.) providing highly accurate line positions and mass spectral data, which aids in identifying complexes.

In addition to frontline antibiotics, this three component delivery system can be used with less utilized antibiotics in the global struggle dealing with *M. tuberculosis*. β-lactam antibiotics are a broad class of antibiotics that are characterized by containing the unique β-lactam ring. The ring contains four atoms (three carbon and one nitrogen atom) as well as a carbonyl functional group. Many of the β-lactam antibiotics interrupt cell wall synthesis therefore inhibiting growth of bacteria. The penicillin-binding proteins that function as enzymes in the production of peptidoglycan, a significant component of the bacterial cell wall, are a critical component for the mechanism of action. Inhibiting the production of peptidoglycan results in bacterial cell death. Peptidoglycan is a natural polymer that contains both sugars and amino acids and helps form the cell wall. The sugar component is composed of N-acetylglucosamine and N-acetylmuramic acid, and there is a peptide chain containing up to five amino acids attached to the sugar component. Bacteria often develop resistance to β-lactam antibiotics by synthesizing a β-lactamase, an enzyme that attacks the β-lactam ring. To overcome this resistance, β-lactam antibiotics are often given with β-lactamase inhibitors such as clavulanic acid. Clavulanic acid is a β-lactam pharmaceutical agent that inhibits β-lactamase but does not possess antibiotic properties by itself. If administered with some penicillins, it can overcome some antibiotic resistance mechanisms.

β-lactams are used to inactivate *Haemophilus influenza, Moraxella catarrhalis, Escherichia coli, Neisseria gonorrhoeae, Neisseria meningitides* and *Staphylococcus aureus* among other microbes. The penicillin's, representatives of the β-lactam group, not only have well known broad spectrum antibiotic applications, but have also been utilized as anti-tuberculosis agents. Studies have demonstrated that β-lactamase activity determines high resistance to β-lactam antibiotics in certain *Mycobacterium* species. In vitro susceptibility of *M. tuberculosis, M. bovis*, and *M. kansasii* to amoxycillin and ticarcillin in combination with clavulanic acid has been demonstrated. In vitro susceptibility of *M. tuberculosis* to ampicillin, amoxicillin, and imipenem when bound to *M. tuberculosis* penicillin binding proteins has been demonstrated as well. The IFN-γ mediated activation in macrophages is a key component in the immune response of bacterial infections of *M. tuberculosis* and *E. coli*. In vitro data has demonstrated that IFN-γ trafficking of copper transporters can increase bactericidal activity against *E. coli* due to increased levels of copper within phagosomes.

In general, Lipinski's Rule of Five is described as parameters that help determine if a medication with medicinal activity has chemical and physical properties that increase the likelihood of being an orally active drug in humans. These rules are based on the fact that the majority of orally administered drugs are small in size and molar mass, and that they have lipophilic characteristics. This idea helps determine molecular properties that are important in discovering the pharmacokinetics of a medicinal compound such as absorption, distribution, metabolism, and excretion (ADME). Lipinski's Rule of Five focuses on water solubility, and molar mass of a medicinal agent, and can provide an upper limit for the total polar surface area (TPSA) and the minimal number of hydrogen bonds that can be formed. However, achieving the parameters associated with Lipinski's Rules does not indicate pharmaceutical activity.

As part of this discovery process, a large number of calculations based on Quantitative Structure-Activity and Relationships (QSAR) concepts were performed on over one hundred and eighty (180) antibiotic structures and compared to the first and second-line TB drugs. QSAR is the use of powerful quantum chemical calculations, often based in semi-empirical methodology, to calculate chemical (i.e. water solubility, acidity, hydrogen bonding sites) and physical (i.e. total polar surface area, shape and geometry, dipole moment) parameters that can be correlated with known parameters and used to understand or predict medicinal or toxicity factors. The first and second-line anti-tuberculosis drugs that were evaluated in this study using QSAR computational methods included: ethambutol, isoniazid, pyrazinamide, rifampicin, streptomycin, amikacin, kanamycin, rifabutin, capreomycin, viomycin, enviomycin, ciprofloxacin, levofloxacin, moxifloxacin, ofloxacin, para-aminosalicylic acid, ethionamide, prothionamide, cycloserine, terizidone, linezolid, rifapentine, bedaquiline, delamanid, clarithromycin, thiacetazone, penicillin, thionamide, protionamide, clofazimine, amoxicillin, clavulanate acid, thioacetazone, imipenem, delaminid, and cilastatin. The β-lactams evaluated in this study using QSAR computational methods included: ampicillin, amoxicillin, imipenem, ticarcillin, and different forms of penicillins. These calculations performed focused on values that could be correlated with Lipinski's Rule of Five and the binding of the copper ion to the pharmaceutical agents. Specifically, when the copper ion was bound to an antibiotic and/or a saccharide such as glucose or sucrose, whether or not there was an improvement of values that can be correlated with pharmaceutical performance (i.e. log P, number of hydrogen bond donor and acceptors and the TPSA or total polar surface area) were sought. FIGS. 6A and B present sample data and correlations for this large scale computational study. Computational work with various penicillins and other anti-tuberculosis drugs indicates that binding the copper ion to the structure not only causes the species to function like a polarity adaptive molecule, but that it also gives favorable log P (partition coefficient between water and octanol layers in a solvent extraction) values and the bound copper ion blocks sites that may participate in hydrogen bonding (donor or acceptor), suggesting an improvement in its medical efficacy. In summary, using computational methods demonstrated that the key parameters for pharmaceutical activity improved when a copper-antibiotic or a copper-sucrose-antibiotic complex was formed.

One embodiment is a tablet composition comprising of the components: a pharmacologically effective amount of one or more antibiotics; one or more pharmaceutically acceptable components in the form of a saccharide where it is present in an amount from at least about one percent to about fifty percent, inclusive, based on a total mass of the tablet; one or more pharmaceutically acceptable transition metal cations which are present in an amount from at least about one percent to about forty percent, inclusive, based on a total mass of the tablet; pharmaceutically acceptable water soluble polymer where it is present in an amount from at least about five percent to about ninety percent in mass, inclusive, based on a total mass of the tablet; and pharmaceutically acceptable components that may serve as binders; disintegrants; glidants; solvents; lubricants; coatings; and/or other excipients that have a total percent of about forty percent based on a total mass of the tablet.

This Summary of Invention section provides an outline of the preliminary studies with one and two components drug delivery systems and their results. These results warranted further studies for this antibiotic-metal ion-PEG drug delivery system with an additional saccharide component. The three component drug delivery system comprised of the antibiotic-metal cation-saccharide-PEG complexes are the basis for the embodiment in this disclosure and described in detail in the next sections.

DETAILED DESCRIPTION

This disclosure involves a tablet composition that includes three molecular components that improve the efficacy of known antibiotics used in the treatment of pulmonary and extra-pulmonary tuberculosis in a variety of forms including drug resistant infections (i.e. MDR-TB, XDR-TB, TDR-TB). These components include a transition metal cation, a saccharide and a water soluble polymer that contribute to the composition of an antibiotic tablet to serve as a delivery system in a physiological environment and enhance the efficacy of an existing anti-tuberculosis antibiotic.

The first component is a transition metal ion that can bind a nitrogen atom (i.e. in an amine, amide), which are present in all major anti-tuberculosis antibiotics. The cation(s) may also bind to oxygen atoms (i.e. in an alcohol, ether, ester, and/or carbonyl) if present in the antibiotic structure, however binding to nitrogen atoms is thermodynamically favored. The transition metal cation may be a physiologically relevant species such as copper, zinc, iron, or nickel. As an example, copper is discussed because it serves a critical functional role in several proteins at low concentrations but also functions as a biocide at higher concentrations.

Copper ions can form hexavalent complexes, allowing a single copper(II) ion to bind to both a saccharide molecule and an antibiotic molecule. The divalent copper cation is used as a copper(II) chloride dihydrate in the preliminary step(s) of tablet production for this technology. The chloride salt is a strong electrolyte, and the anion is ubiquitous in the physiological environment. Chloride has no other chemical properties (basicity, favorable redox potential, etc.) that negatively impact biochemical processes at the concentrations administered in drugs. The other copper salt anions used include sulfate (basicity), nitrate (may induce redox), hydroxide (cause copper(II) to precipitate), have some chemical characteristics that may induce a negative or undesired reaction. The copper ion can bind nitrogen, which all prominent TB drugs contain. This binding can increase the stability of the drug, perform independently as a biocide, increase log P values, make the molecule a polarity adaptive species, and serve as a delivery platform. When copper is drawn into the bacterium as a nutrient source, it potentially can aid in transporting the drug attached across the membrane. Copper(II) has a high affinity for nitrogen and oxygen atoms which are present in isoniazid ($C_6H_7N_3O$). The cation can also act to minimize hydrogen bonds in the antibiotic by binding and subsequently blocking nitrogen's from unwanted interactions, a favorable trait outlined by Lipinski's Rule of Five.

The second component is a water soluble polymer, which is demonstrated using polyethylene glycol (PEG-3350). A medium sized PEG molecule can form aggregates to enclose and transport drugs in vivo and in vitro, increasing residence times and decreasing the chances of the copper-saccharide-antibiotic complexes attaching to an unwanted target. PEG-3350 is a small enough polymer to have favorable water solubility at body temperature (37 degrees Celsius) but large enough to form aggregates. The polymer forms a loosely packed aggregate that encloses and transports the complex, minimizing or preventing the complex from being hindered by other processes in the body. PEG is widely used in medicinal applications and is considered a very mild antiseptic. It has also been used in numerous published clinical studies as a carrier for pharmaceutical applications.

The third component is a saccharide, and may be a monosaccharide, disaccharide, an oligosaccharide or a combination of different saccharide molecules. This work focuses on using the disaccharide sucrose. Saccharides or sugars in these forms serve several key roles in a physiological environment including one of an energy source and a building block for a polymer. For example, sucrose can be hydrolyzed into two smaller molecules, glucose and fructose. Less complex saccharides are more readily absorbed into the body as they pass through the gastrointestinal tract. In *Mycobacterium* species, the sacB gene encodes for the enzyme levansucrose, which is responsible for the breakdown of sucrose and the production of levans. Levans are polysaccharides built from repeating units of fructose. There is a toxicity associated with sucrose in these bacteria which may be attributed to different effects such as (a) fructose residues blocking or adhering to receptor molecules which alter their function and/or (b) the levans that accumulate over time may impact the periplasm due to their molar mass and size. Sucrose is an energy source for many types of cells, but can be toxic to Mycobacteria, an aspect that provides a level of selectivity which may translate into lower side effects and lower dosages if complexed to an anti-tuberculosis drug.

A full treatment with isoniazid can cost less than fifty USD for a complete regimen, but resistant strains of *M. tuberculosis* may render this regimen ineffective. Since this technology repurposes and improves existing anti-tuberculosis drugs rather than developing a new molecule, this technology not only provides a medical solution but also provides an economical solution to the global TB issue. The three components (water soluble polymer, saccharide, and a transition metal ion) comprising the tablet composition and subsequently a delivery system have a lower cost per gram than the front-line antibiotic used. This detailed description will describe how three component systems can be prepared for pharmaceutical applications, provide analytical data used for structural studies, provide cell line study data, and provide in-depth details of the pharmaceutical efficacy of the three component complex. A synopsis of manufacturing and administering the tablet(s) which deliver the three component-antibiotic complex to a patient is outlined as well.

The actual dosage of the drug will depend upon the weight of the patient, the route of administration and the severity of the disease. Slight changes to amounts of components of the tablet will be determined by a health care provider depending on the diagnosis made. For example, isoniazid is used in the treatment of patients with latent and active tuberculosis and the recommended regimen changes with the type of TB present (latent vs. active, resistant vs. nonresistant). Dosage can be correlated with the efficacy of the medicinal agent within a certain toxicity threshold, as described in the context of the embodiment of this invention. Dosages can be correlated and determined, in some cases with the minimum inhibitory concentration, or MIC value, of the pharmaceutical agent. Parameters related to the pharmacokinetic and pharmacodynamic values such as ADME, or its absorption, distribution, metabolism, and excretion, are used in determining these dosages. For antibiotics, a value prescribed for a medicinally appropriate quantity is between five and ten times the MIC value.

The lowering of MIC values, which will be demonstrated and discussed, against active and resistant strains of TB is desirable in drug development. It is well recognized in pharmaceutical practice that the dose given is proportional to a MIC value, and can be calculated using the following equation:

$$\text{Dose}=(C_{max}*V_d)/F \quad (1)$$

Where $C_{max}$ is the highest concentration in blood plasma and is calculated from multiplying the MIC value times two, or:

$$\text{Dose}=(MIC*2*V_d)/F \quad (2)$$

Other parameters to define are $V_d$ which is the volume distribution, and F which is the systemic availability or the fraction of a drug that reaches the blood unaltered. Lowering the MIC value can translate into a lower dosage and lower side effects. When isoniazid is bound to copper and/or sucrose and enclosed by PEG, the F value increases, decreasing the dosage size.

Currently, drug resistant forms of TB are more difficult to impossible to treat with the recommended front-line TB antibiotics, while second-line antibiotics are more expensive and can induce harsh side effects. Currently, there are ten drugs approved by the United States Food and Drug Administration for treating individuals infected with the *M. tuberculosis*. The four primary drugs that are recommended are isoniazid (INH), rifampin (RIF), ethambutol (EMB), and pyrazinamide (PZA). There are variations on the effective administration of these drugs. For example, the primary treatment regimen involves eight weeks of initial treatment in which each drug is given daily totaling over two hundred and twenty pills. The second phase is the continuation phase, which involves daily administration of isoniazid and rifampin for eighteen weeks in which approximately two hundred and fifty pills are given to the patient. A total of over four hundred and fifty pills are given in this standard six month regimen. One issue found internationally is compliance to treatment due to length, number of pills and side effects among other reasons, which has aided in evolution of resistance mechanisms to these antibiotics by the bacterium.

For applications in many medical situations globally it is important to recognize that delivery approach to the patient can be critical for compliance to the prescribed regimen. Combining this unique three component complex with the existing antibiotic and forming it into a tablet is described below for different dosages and different antibiotics. Examples of the three component delivery complexes composed of a saccharide, a copper ion, PEG and the antibiotic are described below, but should not be construed to be in any way limiting for the present invention.

a. Isoniazid is a front-line TB drug that may be given as a tablet in dosages ranging from fifty to three hundred milligrams. As an example of a formulation that represents a 1:1:1:1 molar ratio of the anti-tuberculosis drug as part of the formulation for a fifty milligram dose of isoniazid, the antibiotic would be complexed with 124.8 milligrams of sucrose, 62.04 milligrams of copper (II) chloride dihydrate and 1222.62 milligrams of PEG-3350. Lowering the MIC values for a known drug can result in lower dosages. Experimentally determined MIC values for active TB will be presented below but, as an approximation, if MIC values decrease between five and tenfold, the dose or quantity of the antibiotic administered may decrease five to tenfold. Maintaining the 1:1:1:1 molar ratio, the adjusted quantities could be 10 milligrams of isoniazid, 24.96 milligrams of sucrose, 12.408 milligrams of copper (II) chloride dihydrate, and 244.52 milligrams of PEG-3350.
b. Rifampin is a front-line TB drug that may be given as a capsule in dosages that are one hundred and fifty or three hundred milligrams. As an example of a formulation that represents a 1:1:1:1 molar ratio of the anti-tuberculosis drug as part of the formulation for a one hundred and fifty milligram dose of rifampin, the antibiotic would be complexed with 62.41 milligrams of sucrose, 31.02 milligrams of copper (II) chloride dihydrate and 611.3 milligrams of PEG-3350. Lowering the MIC values for a known drug can result in lower dosages. If MIC values decrease between five and tenfold, the dose or quantity of the antibiotic administered may decrease five to tenfold. Maintaining the 1:1:1:1 molar ratio the adjusted quantities could be 30 milligrams of rifampin, 12.482 milligrams of sucrose, 6.204 milligrams of copper (II) chloride dihydrate, and 122.26 milligrams of PEG-3350.
c. Rifabutin is a TB drug that may be given as a capsule in dosages that are one hundred and fifty milligrams. As an example of a formulation that represents a 1:1:1:1 molar ratio of the anti-tuberculosis drug as part of the formulation for a one hundred and fifty milligram dose of rifabutin, the antibiotic would be complexed with 60.56 milligrams of sucrose, 30.10 milligrams of copper (II) chloride dihydrate and 593.3 milligrams of PEG-3350. Lowering the MIC values for a known drug can result in lower dosages. If the MIC values decrease between five and ten fold, the dose or quantity of the antibiotic administered may decrease five to tenfold. Maintaining the 1:1:1:1 molar ratio the adjusted quantities could be 30 milligrams of rifabutin, 12.12 milligrams of sucrose, 6.02 milligrams of copper (II) chloride dihydrate, and 118.66 milligrams of PEG-3350.
d. Rifapentine is a TB drug that may be given as a tablet in dosages that are one hundred and fifty milligrams. As an example of a formulation that represents a 1:1:1:1 molar ratio of the anti-tuberculosis drug as part of the formulation for a one hundred and fifty milligram dose of rifapentine, the antibiotic would be compounded with 58.49 milligrams of sucrose, 29.076 milligrams of copper (II) chloride dihydrate and 573 milligrams of PEG-3350. Lowering the MIC values for a known drug can result in lower dosages. If MIC values decrease between five and tenfold, the dose or quantity of the antibiotic administered may decrease five to tenfold. Maintaining the 1:1:1:1 molar ratio the adjusted quantities could be 30 milligrams of rifapentine, 11.71 milligrams of sucrose, 5.81 milligrams of copper (II) chloride dihydrate, and 114.6 milligrams of PEG-3350.
e. Pyrazinamide is a TB drug that may be given as a tablet in dosages that are one hundred and fifty or five hundred milligrams. As an example of a formulation that represents a 1:1:1:1 molar ratio of the anti-tuberculosis drug as part of the formulation for a one hundred and fifty milligram dose of pyrazinamide, the antibiotic would be complexed with 417.07 milligrams of sucrose, 207.32 milligrams of copper chloride dihydrate and 40,850 milligrams of PEG-3350. Lowering the MIC values for a known drug can result in lower dosages. If MIC values decrease between five and tenfold, the dose or quantity of the antibiotic administered may decrease five to tenfold. Maintaining the 1:1:1:1 molar ratio the adjusted quantities could be 30 milligrams of pyrazinamide, 83.41 milligrams of sucrose, 41.46 milligrams of copper (II) chloride dihydrate, and 8,170 milligrams of PEG-3350.
f. Ethambutol is a TB drug that may be given as a tablet in dosages that are one-hundred or four-hundred milligrams. As an example of a formulation that represents a 1:1:1:1 molar ratio of the anti-tuberculosis drug as part of the formulation for a 100 milligram dose of ethambutol, the antibiotic would be complexed with 167.40 milligrams of sucrose, 83.21 milligrams of copper (II) chloride dihydrate and 1,640 milligrams of PEG-3350. Lowering the MIC values for a known drug can result in lower dosages. If MIC values decrease between five and tenfold, the dose or quantity of the antibiotic administered may decrease five to tenfold. Maintaining the 1:1:1:1 molar ratio the adjusted quantities could be 20 milligrams of ethambutol, 33.48 milligrams of sucrose, 16.66 milligrams of copper (II) chloride dihydrate, and 328 milligrams of PEG-3350.
g. Cycloserine is a TB drug that may be given as a capsule in dosages that are two hundred and fifty milligrams. As an example of a formulation that represents a 1:1:1:1 molar ratio of the anti-tuberculosis drug as part of the formulation for a two hundred and fifty milligram dose of cycloserine, the antibiotic would be complexed with 838.2 milligrams of sucrose, 416.66 milligrams of copper (II) chloride dihydrate and 8211 milligrams of PEG-3350. Lowering the MIC values for a known drug can result in lower dosages. Experimentally determined MIC values for active TB will be presented below but, as an approximation, if MIC values decrease between five and tenfold, the dose or quantity of the antibiotic administered may decrease five to tenfold. Maintaining the 1:1:1:1 molar ratio the adjusted quantities could be 50 milligrams of cycloserine, 166.44 milligrams of sucrose, 83.33 milligrams of copper (II) chloride dihydrate, and 1642.2 milligrams of PEG-3350.

h. Ethionamide is a TB drug that may be given as a tablet in dosages that are two hundred and fifty milligrams. As an example of a formulation that represents a 1:1:1:1 molar ratio of the anti-tuberculosis drug as part of the formulation for a two hundred and fifty milligram dose of ethionamide, the antibiotic would be complexed with 515.04 milligrams of sucrose, 256.02 milligrams of copper (II) chloride dihydrate and 5045 milligrams of PEG-3350. Lowering the MIC values for a known drug can result in lower dosages. If MIC values decrease between five and tenfold, the dose or quantity of the antibiotic administered may decrease five to tenfold. Maintaining the 1:1:1:1 molar ratio the adjusted quantities could be 50 milligrams of ethionamide, 103.008 milligrams of sucrose, 51.204 milligrams of copper (II) chloride dihydrate, and 1009 milligrams of PEG-3350.

i. Streptomycin is a TB drug that may be given as an aqueous solution for intravenous or intramuscular administration in dosages that are one gram vials. As an example of a formulation that represents a 1:1:1:1 molar ratio of the anti-tuberculosis drug as part of the formulation for a one thousand milligram dose of streptomycin, the antibiotic would be compounded with 588.64 milligrams of sucrose, 292.59 milligrams of copper chloride dihydrate and 5766 milligrams of PEG-3350. Lowering the MIC values for a known drug can result in lower dosages. If MIC values decrease between five and tenfold, the dose or quantity of the antibiotic administered may decrease five to tenfold. Maintaining the 1:1:1:1 molar ratio the adjusted quantities could be 200 milligrams of streptomycin, 117.72 milligrams grams of sucrose, 58.52 milligrams of copper (II) chloride dihydrate, and 1153.2 milligrams of PEG-3350.

j. Amikacin is a TB drug that may be given as an aqueous solution for intravenous or intramuscular administration in dosages that are one gram. As an example of a formulation that represents a 1:1:1:1 molar ratio of the anti-tuberculosis drug as part of the formulation for a 1000 milligram dose of amikacin, the antibiotic would be complexed with 584.61 milligrams of sucrose, 290.59 milligrams of copper (II) chloride dihydrate and 5726 milligrams of PEG-3350. Lowering the MIC values for a known drug can result in lower dosages. If MIC values decrease between five and tenfold, the dose or quantity of the antibiotic administered may decrease five to tenfold. Maintaining the 1:1:1:1 molar ratio the adjusted quantities could be 200 milligrams of streptomycin, 117.72 milligrams grams of sucrose, 58.52 milligrams of copper (II) chloride dihydrate, and 1153.2 milligrams of PEG-3350.

k. Capreomycin is a TB drug that may be given as an aqueous solution for intravenous or intramuscular administration in dosages that are one gram vials. As an example of a formulation that represents a 1:1:1:1 molar ratio of the anti-tuberculosis drug as part of the formulation for a 1000 milligram dose of capreomycin, the antibiotic could be compounded with 511.97 milligrams of sucrose, 254.49 milligrams of copper (II) chloride dihydrate and 5015 milligrams of PEG-3350. Lowering the MIC values for a known drug can result in lower dosages. If MIC values decrease between five and tenfold, the dose or quantity of the antibiotic administered may decrease five to tenfold. Maintaining the 1:1:1:1 molar ratio the adjusted quantities could be 200 milligrams of capreomycin, 102.39 milligrams grams of sucrose, 50.89 milligrams of copper (II) chloride dihydrate, and 1003.0 milligrams of PEG-3350.

l. p-Aminosalicylic acid (PAS) is a TB drug that may be given as an aqueous solution for intravenous administration. A four gram dose, given twice a day is often prescribed. As an example of a formulation that represents a 1:1:1:1 molar ratio of the anti-tuberculosis drug as part of the formulation for a 4,000 milligram dose of p-aminosalicyclic, the antibiotic would be compounded with 8,941 milligrams of sucrose, 4,444.4 milligrams of copper chloride dehydrate and 87,582 milligrams of PEG-3350. Lowering the MIC values for a known drug can result in lower dosages. If MIC values decrease between five and tenfold, the dose or quantity of the antibiotic administered may decrease five to tenfold. Maintaining the 1:1:1:1 molar ratio the adjusted quantities could be 800 milligrams of PAS, 1,788.2 milligrams grams of sucrose, 888.8 milligrams of copper (II) chloride dihydrate, and 17,516 milligrams of PEG-3350.

m. Penicillin-G, representing the beta-lactams, is rarely used as a tuberculosis drug but its performance may be enhanced using this three component approach. A one hundred milligram dose is proposed as a starting point considering published preclinical trial data. As an example of a formulation that represents a 1:1:1:1 molar ratio of the anti-tuberculosis drug as part of the formulation, the antibiotic would be compounded with 99.11 milligrams of sucrose, 50.56 milligrams of copper (II) chloride dihydrate and 994.06 milligrams PEG-3350. Lowering the MIC values for a known drug can result in lower dosages. If MIC values decrease between five and tenfold, the dose or quantity of the antibiotic administered may decrease five to tenfold. Maintaining the 1:1:1:1 molar ratio the adjusted quantities could be 20 milligrams of penicillin, 19.82 milligrams of sucrose, 10.11 milligrams of copper (II) chloride dihydrate, and 198.81 milligrams of PEG-3350.

n. A combination of antibiotics including isoniazid (INH), rifampicin (RIF), pyrazinamide (PZA) and ethambutol (EMB) are considered the front-line TB drugs and are used together as the standard regimen to treat TB. 75 milligrams or 0.00054 moles of isoniazid, 400 milligrams or 0.00031 moles of pyrazinamide, 275 milligrams or 0.00074 moles of ethambutol, and 150 milligrams or 0.000180 moles of rifampicin are often the dosages prescribed to treat TB patients. Considering the combined number of moles for the four antibiotics, 0.00177 moles, the following is a molar ratio formulation that includes four antibiotics and the three additional drug delivery components (INH:PYR:ETH:RIF:Cu:SUC:PEG) would be (0.54:0.31:0.74:0.180:10.62:7.08:0.885). The total molar amount of sucrose is a 1:1 molar ratio with the total number of moles for the four antibiotics, while the copper ion is a 3:1 molar ratio because some of the antibiotics have more than one nitrogen atom. This ensures that all of the antibiotics can have at least one copper ion bound to an amine, while a larger species with several nitrogen atoms (i.e. RIF) would likely have two copper ions. This will also increase aggregation between the molecules via ion dipole interactions and hydrogen bonds. The PEG-3350 component is added at a 1:2 ratio (moles of PEG:moles antibiotics) for the moles of polymer to total moles of antibiotics. Because the copper ions, antibiotics and disaccharide are bound together and entrapped in a loose aggregate, less PEG is required, lowering its mass percentage.

While the sample formulations utilize different molar ratios of the three components, the antibiotic(s), and the other components, specific values are varied to optimize the treatment procedure. For example, PEG can retain water at a ratio of up to three water molecules per ethanol unit ($-CH_2-CH_2-O-$), so the molar ratio of PEG may decrease to 0.1 to 0.2 per antibiotic molecule in some cases. Likewise, copper is a hexavalent species and can bind two or three antibiotic molecules and/or saccharides in some cases per ion (i.e. $Cu(INH)_2$, $Cu(SUC)_2$) or form an antibiotic-saccharide complex (i.e. $Cu_1(INH)_1(SUC)_1$) so its molar ratio may, in some cases, be lowered. Likewise, some antibiotics contain multiple nitrogen atoms that can bind more than a single copper ion, and therefore may create instances in which the moles of copper ion need to be greater than the moles of the antibiotic. Antibiotics with more than one or two nitrogen and/or oxygen atoms in their structure, such as capreomycin ($C_{25}H_{14}H_{14}O_8$) may require additional copper ions to minimize unwanted hydrogen bonding to stabilize its structure. Decreasing or increasing the moles of the components of the drug delivery system may decrease or increase the quantities of the components added, therefore altering the total milligrams of the tablet.

Computational work associated with this disclosure has shown that important values outlined by Lipinski's Rule of Five are maintained or improved in these complexes. For example, log P (log of the partition coefficient for the distribution of a species between water and octanol layers in a glass vessel) for $[Cu(INH)_2(H_2O)_2]^+$ is similar to that of the monodentate ligand complex ($Cu(INH)_1$). Likewise, the Total Polar Surface Area (TPSA) remains below the threshold set by Lipinski's rules for bi and tridentate complexes for many of the antibiotic and/or saccharide complexes.

In addition, the preparation of a tablet would include other inert compounds such as microcrystalline cellulose, colloidal silica, hydroyxypropyl methylcellulose, magnesium stearate, sodium ascorbate, suspended silicon dioxide, purified water and a basic coating premix yellow and/or red. These excipients and others may serve as binders, disintegrates, glidants, lubricants, solvents, and/or coatings. The coating procedure may be performed below fifty degrees Celsius and with a specific spray varying between twenty and one hundred and twenty grams per kilogram of the compressed phases. Once the mixture is prepared, it can be made into tablets with masses equal to or less than 1.5 grams but may be as low as three hundred milligrams.

The present invention includes a more detailed process for the tablet preparation, that should not be construed in any way as to limit the present invention, is described as:
(i) Mixing the active ingredient, an antibiotic, with a specified molar ratio of copper (II) chloride dihydrate, a molar ratio of a saccharide such as sucrose, and a molar ratio of a water soluble polymer such as polyethylene glycol in a high shear mixer.
(ii) Adding one or more binders such as crystalline cellulose in the same high shear mixer.
(iii) Adding a solvent such as highly purified water, to expose the composition to a dissolving environment in the same high shear mixer.
(iv) Adding a lubricant such as magnesium stearate in the same high shear mixer.
(v) Adding a glidant such as suspended silicon dioxide in the same high shear mixer.
(vi) Adding sodium ascorbate or ascorbic acid as an anti-oxidant in the same high shear mixer.
(vii) Excess water would be removed in a dehydration step.
(viii) A tablet would be made by compression in a tablet press to a size not to exceed eleven millimeters in diameter and a mass not to exceed two thousand milligrams but preferably below twelve hundred milligrams.
(ix) Coating would take place in a pan coater such as those manufactured by Glatt.

Another example would include the manufacturing of a tablet that contains more than one antibiotic. An example of this production, that should not be construed in any way as to limit the present invention, is outlined:
(i) Mixing the active ingredients, the antibiotics, with a specified molar ratio of copper (II) chloride, a molar ratio of a saccharide such as sucrose, and a molar ratio of a water soluble polymer such as polyethylene glycol in a high shear mixer. The antibiotics would consist of a mixture of isoniazid, rifampicin, pyrazinamide and/or ethambutol.
(ii) Adding one or more binders such as crystalline cellulose in the same high shear mixer.

Analytical studies such as NMR help provide a model that includes the following structural features: (a.) the copper ion binds the isoniazid via nitrogen, oxygen and pi bonds in the isoniazid molecule (b.) the copper ion binds sucrose via various oxygen atoms (c.) when copper, isoniazid and sucrose are aggregated by PEG there is a complexation effect between copper, isoniazid and sucrose while there is only a weak interaction between the copper, isoniazid, sucrose and the PEG aggregate.

As outlined previously in this discovery two component (i.e. copper(II), PEG) systems involving first and second-line antibiotics (i.e. rifampicin, capreomycin, amikacin) demonstrated that in some cases these components, as either individual chemical species or as a combination, can increase the efficacy of the antibiotics against active and resistant strains of TB. Further testing consists of the three component delivery system composed of copper(II), PEG, and sucrose is described below.

Four different combinations of compounds including the frontline antibiotic isoniazid, sucrose, copper(II) ion, and the biopolymer PEG-3350 were tested against the *M. tuberculosis* H37Rv strain, through a program sponsored by the National Institutes of Health—National Institute of Allergy and Infectious Disease (NIH-NIAID). Minimum inhibition concentrations (MIC), inhibition concentrations (IC), minimum bactericidal activity (MBC), and intracellular activity were found in aerobic and low oxygen conditions.

In order to understand the significance of this invention, it is important to outline experimental procedures in which the compounds in different variations were tested against *M. tuberculosis*. Compounds were removed from a negative twenty degrees Celsius system, warmed to room temperature, and reweighed before solubilization in diemthylsulfoxide (DMSO). Compounds were solubilized in DMSO to a concentration of ten micromolar. Assays were initiated within seven days of solubilization. Compounds were dispensed into ninety-six-well plates using a BioMek 3000 and serial dilutions were prepared. Dilutions were dispensed into final assay plates for each task.

The MIC of each compound was determined by measuring bacterial growth after five days in the presence of test compounds. Compounds were prepared as twenty-point two-fold serial dilutions in DMSO and diluted into 7H9-Tw-OADC medium in ninety-six-well plates with a final DMSO concentration of two percent. The highest concentration of compound was two hundred micromolars where compounds were soluble in DMSO at ten millimolar. For compounds with limited solubility, the highest concentration was fifty times less than the stock concentration (e.g. one hundred micromolar for five millimolar DMSO stock, twenty micromolar for one millimolar DMSO stock). Control compounds were prepared as ten-point two-fold dilution series. Each plate included assay controls for background (medium/DMSO only, no bacterial cells), zero growth (one hundred micromolar isoniazid) and maximum growth (DMSO only), as well as an isoniazid dose response curve. Plates were inoculated with *Mycobacterium tuberculosis* and incubated for five days: growth was measured by optical density at five hundred and ninety nanometers and fluorescence (Excitation at 560 nm/Emission at 590 nm) using a plate reader. Growth values were calculated separately for $OD_{590}$ and relative fluorescence units (RFU). To calculate the MIC value, the dose response curve was plotted as percent (%) growth and fitted to the Gompertz model.

The MIC value is defined as the minimum concentration at which growth was completely inhibited and was calculated from the inflection point of the fitted curve to the lower asymptote (zero growth). In addition, dose response curves were generated using the Levenberg-Marquardt algorithm and the concentrations that resulted in fifty percent and ninety percent inhibition of growth were determined ($IC_{50}$ and $IC_{90}$ respectively). As an example, raw data provided in table two can be used to plot either type of curve.

TABLE 2

Sample RFU and OD measurements used to determine MIC values for various complexes.

| Concentration (μM) | % Growth (RFU) | % Growth (OD) |
| --- | --- | --- |
| 200 | 3 | 5 |
| 100 | 3 | 4 |
| 50 | 3 | 5 |
| 25 | 3 | 5 |
| 12.5 | 3 | 5 |
| 6.3 | 3 | 5 |
| 3.1 | 3 | 5 |
| 1.6 | 4 | 6 |
| 0.78 | 24 | 31 |
| 0.39 | 79 | 95 |
| 0.20 | 91 | 109 |
| 0.10 | 94 | 108 |
| 0.050 | 95 | 107 |
| 0.025 | 96 | 106 |
| 0.013 | 94 | 108 |
| 0.0063 | 98 | 105 |
| 0.0031 | 96 | 106 |
| 0.0016 | 99 | 104 |
| 0.00078 | 97 | 106 |
| 0.00039 | 96 | 105 |
| 200 | 3 | 5 |
| 100 | 3 | 4 |
| 50 | 3 | 5 |
| 25 | 3 | 4 |
| 12.5 | 3 | 4 |
| 6.3 | 3 | 4 |

TABLE 2-continued

Sample RFU and OD measurements used to determine MIC values for various complexes.

| Concentration (μM) | % Growth (RFU) | % Growth (OD) |
| --- | --- | --- |
| 3.1 | 3 | 5 |
| 1.6 | 4 | 5 |
| 0.78 | 38 | 44 |
| 0.39 | 72 | 90 |
| 0.20 | 93 | 103 |
| 0.10 | 98 | 105 |
| 0.050 | 99 | 104 |
| 0.025 | 96 | 105 |
| 0.013 | 98 | 102 |
| 0.0063 | 99 | 103 |
| 0.0031 | 98 | 101 |
| 0.0016 | 98 | 100 |
| 0.00078 | 99 | 103 |
| 0.00039 | 99 | 106 |
| 200 | 1 | 2 |
| 100 | 2 | 2 |
| 50 | 3 | 4 |
| 25 | 3 | 4 |
| 12.5 | 3 | 5 |

The antimicrobial activity of compounds against *M. tuberculosis* H37Rv grown under hypoxic conditions was assessed using the low oxygen recovery assay (LORA) (see table three). Bacteria are first adapted to low oxygen conditions and then exposed to compounds under hypoxia; this is followed by a period of outgrowth in aerobic conditions and growth is measured using luminescence. Most antibiotic screening involves bacteria that are replicating. *M. tuberculosis* can exist in an inactive state referred to as nonreplicating persistence (NRP). There is now substantial evidence reported in the scientific literature that this state may be responsible for the long pharmaceutical regimens patients endure in the treatment of tuberculosis. The LORA protocol was developed and is now implemented on a wide scale to test compounds for activity against bacteria in the NRP state.

(iii) Adding a solvent such as highly purified water, to expose the composition to a dissolving environment in the same high shear mixer.

(iv) Adding a lubricant such as magnesium stearate in the same high shear mixer.

(v) Adding a glidant such as suspended silicon dioxide in the same high shear mixer.

(vi) Add sodium ascorbate or ascorbic acid as an antioxidant in the same high shear mixer.

(vii) Excess water would be removed in a dehydration step.

(viii) A tablet composed of all the components would be made by compression in a tablet press in a size not to exceed eleven millimeters and a mass not to exceed two thousand milligrams but preferably below twelve hundred milligrams.

(ix) Coating would take place in a pan coater such as those manufactured by Glatt.

PEG-3350 is a water soluble polymer that is widely used as a laxative. A typical dosage is seventeen grams dissolved in water. The pharmaceutical quantities outlined above all lie significantly below this value giving an example of its lack of toxicity. Additionally, the sucrose quantities do not approach toxicity levels. For example, the $LD_{50}$ (mg/kg) level of sucrose is 29,700 which is much higher than ethyl alcohol at 14,000, sodium chloride (common table salt) at 3,000, vitamin A at 2,000, vanillin at 1,580 and aspirin at 1,000 which are all consumed on a regular basis. There may be concerns about the toxicity of copper being used in a medicine. The $LD_{50}$ for copper gluconate, which is used to treat copper deficiency, is 1710 mg/kg for rats (oral) whereas the $LD_{50}$ for copper (II) chloride is 140 mg/kg for rats (oral) demonstrating the impact that binding the copper ion to a chelating agent can have on its toxicity. In most cases a chelating agent is a species that binds the cation via covalent, ionic, and/or ion dipole interactions. For further explanation, the species EDTA or ethylenediaminetetraacetic acid is a well-known chelating agent that can bind an ionic species such as copper(II), nickel(II), iron(II) or zinc(II) via interactions involving its amines (i.e. copper-nitrogen) and/or its carboxylates (—COO⁻-copper(II)).

In this embodiment the copper ion binds to the nitrogen (and/or oxygen atoms if present, e.g. isoniazid) in the antibiotic and to the oxygen present in the sucrose molecule while being enclosed in the PEG aggregate. Two milligrams of copper per day is the minimum requirement for an adult. The value of copper intake of 0.5 milligrams per kilogram body weight, or fifty milligrams for a one hundred kilogram person is recommended. Animal toxicity with copper salts was observed only with quantities several orders of magnitude greater than that used as food supplements. In addition, most copper in the body is bound to proteins and is critical for physiological processes. Unbound copper ions are the potentially toxic species, while bound or trapped copper have a significantly lower toxicity in the human body.

The geometry of the tablet is an important parameter in producing an oral medication. A recent document entitled "Size, Shape, and Other Physical Attributes of Generic Tablets and Capsules. Guidance for Industry" released by U.S. Department of Health and Human Services Food and Drug Administration, Center for Drug Evaluation and Research (CDER) in June 2015, provides an outline for tablet dimensions. The three component delivery complex and the antibiotic described here would have a typical density range between 1.2 and 1.7 grams per centimeter cubed. Currently, isoniazid tablets have several forms. For example, the isoniazid 100 Ver are round, white tablets imprinted with "Westward" and "260" on opposite sides. The isoniazid 100 mg-BAR is a round, white tablet and the isoniazid 300 mg-BAR is an oval, white tablet. Isoniazid 300 mg-VER is round, white and imprinted with "WestWard" and "261" on opposite sides. Using the proposed formulation of a fifty milligram dose of isoniazid complexed with 124.8 milligrams of sucrose, 62.04 milligrams of copper (II) chloride dihydrate and 1222.62 milligrams of PEG-3350, results in a total mass of approximately 1460 milligrams and an approximate density of 1.5 grams per centimeter cubed, depending on the exact conditions under which the tablet was formed. If the correction outlined above taking into account the lower MIC values and subsequently a lower dosage is utilized, this value may decrease to 0.3 centimeters cubed. If additional species are added such as the lubricant magnesium stearate, and a glidant such as silicon dioxide, the tablet would have a total volume of 1.0 centimeter cubed and a mass of 1.5 grams. Considering the FDA recommended size of eight millimeters (0.8 cm), this mass may be divided over five equal mass and volume shaped sized tablets for a single dose, as an example of the tablet production that should not be construed to be limiting in any way to the present invention.

Proton ($^1$H) and carbon ($^{13}$C) NMR was used to study the copper-glucose-PEG-isoniazid and the copper-sucrose-PEG-isoniazid complexes and their subcomponents to understand the types of interactions and bonding that exists between the different components (see table one). This structural knowledge helps illustrate the manner in which the aggregate and its contents can perform as a delivery agent, perform as a nutrient source, how the toxicity of the copper(II) ion might be minimized, how isoniazid functions as a prodrug, how the copper(II) ion binds isoniazid or sucrose, and the interactions between the four components. First, the NMR spectral features of the pure organics (glucose, sucrose, isoniazid, PEG) were measured by proton ($^1$H) and carbon ($^{13}$C) NMR. These studies were followed by the NMR measurements of copper(II) complexed to each of the organics (i.e. copper-isoniazid, copper-sucrose, copper-PEG, and isoniazid-copper-sucrose). Copper(II) chloride is paramagnetic and the binding of the cation to nitrogen and/or oxygen atoms can impact the NMR spectral line position, its full width half maximum and in some cases, whether it can be observed at all. For example, figure seven shows the $^{13}$C NMR for pure isoniazid, which shows the four peaks for the four carbon species in different environments. Figure eight provides the $^{13}$C NMR spectra for the copper-isoniazid complex and illustrates the impact that the paramagnetic species has on the $^{13}$C spectra showing a loss of spectral features. The fact that the spectral features associated with all four carbon atoms in the isoniazid molecule were impacted by the binding to the copper ion indicates the complex is a polarity adaptive molecule or the copper ion moves around the molecule, binding to pi bonds, oxygen and nitrogen molecules.

TABLE 1

The spectral positions (ppm) for the proton ($^1$H) and carbon ($^{13}$C) NMR datum of isoniazid complexes and their subcomponents. (ppm is parts per million and represents chemical shifts of the resonant frequency in the magnetic field of the nucleus).

| Compounds | $^1$H NMR (ppm) | $^{13}$C NMR (ppm) |
|---|---|---|
| Isoniazid | 4.8 ppm, 7.5 ppm, 8.5 ppm | 167 ppm, 149 ppm, 140 ppm, 121 ppm |
| Glucose | 3.1 ppm, 3.3 ppm, 3.65 ppm, 4.55 ppm, 5.2 ppm | 61 ppm, 69 ppm, 72 ppm, 73 ppm, 74 ppm, 76 ppm, 92 ppm, 96 ppm |
| PEG-3350 | 3.65 ppm | 69 ppm |
| Cu(II)-PEG-3350 | 3.65 ppm, 4.8 ppm | 69 ppm |
| Cu(II)-Glucose | Spectral feature stretching from 4 ppm to 5.5 ppm, and other features at 3.2 ppm and 3.6 ppm. | 61 ppm, 71 ppm, 72 ppm, 73 ppm, 74 ppm, 76 ppm, 96 ppm |
| Cu(II)-Isoniazid | 4.8 ppm | No observable spectral features |
| Cu(II)-PEG-Glucose-Isoniazid | 3.65 ppm, 4.65 ppm | 69 ppm |

TABLE 3

Raw data used for LORA measurements (RLU is relative light units or relative luminescence units).

| Oxygen Tension | Concentration (μM) | Growth (RLU) |
|---|---|---|
| Low Oxygen | 200 | 13 |
| | 100 | 18 |
| | 50 | 21 |
| | 25 | 15 |
| | 12.5 | 19 |
| | 6.3 | 26 |
| | 3.1 | 42 |
| | 1.6 | 82 |

TABLE 3-continued

Raw data used for LORA measurements (RLU is relative light units or relative luminescence units).

| Oxygen Tension | Concentration (μM) | Growth (RLU) |
|---|---|---|
|  | 0.78 | 112 |
|  | 0.39 | 1950 |
|  | 0.20 | 6980 |
|  | 0.10 | 6840 |
|  | 0.05 | 6920 |
|  | 0.025 | 7120 |
|  | 0.013 | 7150 |
|  | 0.0063 | 7100 |
|  | 0.0031 | 7000 |
|  | 0.0016 | 7250 |
|  | 0.00078 | 7020 |
|  | 0.00039 | 7120 |
| Normal Oxygen | 200 | 75 |
|  | 100 | 40 |
|  | 50 | 30 |
|  | 25 | 41 |
|  | 12.5 | 74 |
|  | 6.3 | 53 |
|  | 3.1 | 51 |
|  | 1.6 | 62 |
|  | 0.78 | 74 |
|  | 0.39 | 74 |
|  | 0.20 | 22300 |
|  | 0.10 | 23200 |
|  | 0.05 | 23600 |
|  | 0.025 | 24400 |
|  | 0.013 | 25400 |
|  | 0.0063 | 23600 |
|  | 0.0031 | 25100 |
|  | 0.0016 | 22100 |
|  | 0.00078 | 25800 |
|  | 0.00039 | 25500 |

The MIC values measured under low oxygen were prepared as twenty-point two-fold serial dilutions in DMSO and diluted into DTA medium in ninety-six well plates with a final DMSO concentration of two percent. The highest concentration of compound was two hundred micromolar where compounds were soluble in DMSO at ten millimolar. For compounds with limited solubility, the highest concentration was fifty times less than the stock concentration, for example one-hundred micromolar for a five millimolar DMSO stock solution, twenty micromolar for a one millimolar DMSO stock solution. Control compounds were prepared as ten-point, two-fold serial dilutions in DMSO and diluted into DTA medium in ninety-six-well plates with a final DMSO concentration of two percent.

M. tuberculosis constitutively expressing the luxABCDE operon was inoculated into DTA medium in gas-impermeable glass tubes and incubated for eighteen days to generate hypoxic conditions (follows the Wayne model of hypoxia). At this point, bacteria are in a non-replicating state (NRP stage two) induced by oxygen depletion.

Oxygen-deprived bacteria were inoculated into compound assay plates and incubated under anaerobic conditions for ten days followed by incubation under aerobic conditions (outgrowth) for five days. Growth was measured by luminescence. Oxygen-deprived bacteria were also inoculated into compound assay plates and incubated under aerobic conditions for five days. Growth was measured by luminescence. Rifampicin was included in each plate and metronidazole was included in each run as positive controls for aerobic and anaerobic killing of M. tuberculosis, respectively.

The bactericidal activity of compounds was assessed against M. tuberculosis H37Rv grown in aerobic conditions in 7H9-Tw-OADC medium. Viable cell counts were measured over three weeks of exposure to determine the rate of kill.

M. tuberculosis was grown aerobically to logarithmic phase and inoculated into the liquid medium containing four different compound concentrations with a final maximum concentration of two percent DMSO. For compounds with an MIC value (from group assay), the concentrations selected were ten times the MIC value, five times the MIC value, one time the MIC value, and one-quarter the MIC value. Cultures were exposed to compounds for twenty-one days and cell viability is measured by enumerating colony forming units (CFU's) on agar plates on day zero, seven, fourteen and twenty-one. MIC values were calculated as the average of the MIC value derived from the Relative Fluorescence Unit and OD from assay group one.

The general definition of the minimum bactericidal concentration, or MBC, is the minimum concentration of an antibacterial chemical species required to kill a specific bacterium. In this study or evaluation of anti-tuberculosis complexes, the MBC is defined as the minimum concentration required achieving a two-log kill in twenty-one days. For compounds with a greater than one-log kill, an assessment of time and/or concentration-dependence was determined from the kill kinetic measurements. A DMSO solution was used as a positive control for growth.

The cytotoxicity of the compounds and controls towards eukaryotic cells was determined using the Vero African green monkey kidney cell line. Vero cells were incubated with compounds for two days, and the cell viability was measured. The $IC_{50}$ is determined as the concentration of compound causing a fifty percent loss in viability. The intracellular activity of compounds is measured using a macrophage cell line infected with M. tuberculosis. Murine macrophages are infected with bacteria and viable bacterial counts measured over four days using luminescence as a measure of growth—a linear relationship between the colony forming units and luminescence was established.

The cytotoxicity of both the novel medicinal compounds and the controls was determined by measuring the Vero cell viability growth after two days in the presence of test compounds. Compounds were prepared as ten-point three-fold serial dilutions in DMSO. Vero cells were cultured in DMEM containing high glucose and GlutaMAX™, ten percent FBS, and a penicillin-streptomycin solution. Cells were inoculated into assay plates and cultured for twenty four hours before compound dilutions were added to a final DMSO concentration of one percent. The highest concentration of compound tested was one hundred micromolar where compounds were soluble in DMSO at ten millimolar. For compounds with limited solubility, the highest concentration was fifty times less than the stock concentration; for example a one hundred micromolar solution from a five millimolar DMSO stock, twenty micromolar for a one millimolar DMSO stock. Each plate included staurosporine as a control. Staurosporine is an antibiotic that is a natural product extracted from the microbe Streptomyces staurosporeus. The pharmaceutical activity of staurosporine involves the inactivation of protein kinases by preventing ATP from interacting with the kinase. Staurosporine binds the site stronger than ATP does. Staurosporine is not very selective as to which kinase it binds, but it does bind them with a strong bond.

Assay plates were incubated for two days at thirty-seven degrees Celsius in a five percent carbon dioxide atmosphere, growth was measured using a Luminescent Cell Viability Assay which uses ATP as an indicator of cell viability.

Relative luminescent units (RLU) were measured using a plate reader. The dose response curve was fitted using the Levenberg-Marquardt algorithm. The Levenberg-Marquardt algorithm is also called the damped least-squares approach, and is utilized to solve problems that involve non-linear least squares which arrive in treating data that involves curve fitting. The $TC_{50}$ was defined as the compound concentration that produced fifty percent inhibition of growth. *M. tuberculosis* resides in macrophages, making treating the infection difficult. This encapsulation can protect the bacterium from both antibiotic and natural treatment. The protection of the macrophage can provide a long term reservoir of the microbe in a patient. The following is the protocol used to measure intracellular activity of isoniazid.

Murine J774 macrophages were infected with a luminescent strain of H37Rv (which constitutively expresses lux-ABCDE) at a multiplicity of infection of one. After eighteen hours, extracellular bacteria were removed by washing and the compound was added. The infected macrophages were incubated in the presence of compound for four days at one time and ten times the MIC (as determined in aerobic culture in liquid medium from Task 1 outlined above).

Bacteria were harvested from macrophages by lysis with one tenth of a percent sodium dodecyl sulfate (SDS), inoculated into growth media and allowed to grow aerobically for five days, at which time the quantity of bacteria present was determined by luminescence. All assays were conducted in triplicate; each assay included a positive control (four micromolar isoniazid) and a negative control (two percent DMSO). The intracellular activity was expressed as a log reduction of *M. tuberculosis* using the formula:

$$[\text{Log (RLU Day 4 Compound)}]-[\text{Log (RLU Day 4 DMSO)}] \quad (3)$$

As a control for each assay, the inoculum was plated into ninety-six-well plates, grown for five days and luminescence measured; correlation of RLU and CFU was confirmed for each run. The baseline of infection was determined by harvesting bacteria from macrophages at day zero before compound addition and plating for colony formation units determination in triplicate.

The activity of the three component carrier and its subcomponents were tested against five resistant isolates of *M. tuberculosis* strains under aerobic conditions and was assessed by determining the minimum inhibitory concentration (MIC) of each compound. Strains tested were two isoniazid resistant strains (INH-R1 and INH-R2), two rifampicin resistant strains (RIF-R1 and RIF-R2) and a fluoroquinolone resistant strain (FQ-R1). The assay is based on measurement of growth in liquid medium of each strain where the readout is optical density (OD). INH-R1 was derived from H37Rv and is a katG mutant (Y155*=truncation). INH-R2 is strain ATCC35822. RIF-R1 was derived from H37Rv and is an rpoB mutant (S522L). RIF-R2 is strain ATCC35828. FQ-R1 is a fluoroquinolone-resistant strain derived from H37Rv and is a gyrB mutant (D94N).

The activity of the three component carrier and its subcomponents, referred to as compounds, was demonstrated with MIC values of the compound and were determined by measuring bacterial growth after five days in the presence of compounds. Compounds were prepared as twenty-point two-fold serial dilutions in DMSO and diluted into 7H9-Tw-OADC medium in ninety-six-well plates with a final DMSO concentration of two percent. The highest concentration of compound was two hundred micromolar where compounds were soluble in DMSO at ten millimolar. For compounds with limited solubility, the highest concentration was fifty times less than the stock concentration; for example one hundred micromolar for a five millimolar DMSO stock, twenty micromolar for one millimolar DMSO stock. Plates were inoculated with *M. tuberculosis* and incubated for five days; growth was measured by $OD_{590}$. To calculate the MIC, the ten-point dose response curve was plotted as percent growth and fitted to the Gompertz model. The Gompertz growth model is frequently utilized when analyzing data plotted on a two dimensional graph, and functions best when the plotted data set is a smooth curve.

From a graphical perspective, the MIC is the minimum concentration at which growth was completely inhibited and is calculated from the inflection point of the fitted curve to the lower asymptote (zero growth). The dose response curves are generated using the Levenberg-Marquardt algorithm and the concentrations that resulted in fifty percent and ninety percent inhibition of growth were determined ($IC_{50}$ and $IC_{90}$ respectively). Raw data is provided and can be used to plot either type of curve.

Data resulted from testing various compounds including isoniazid, copper(II), sucrose, and PEG-3350 against resistant and nonresistant stains of *M. tuberculosis* are now presented and discussed. The front-line anti-tuberculosis drug isoniazid was used to demonstrate the three component system in a number of experiments. Figure nine shows graphical data for the determination of the MIC, $IC_{50}$ and $IC_{90}$ values for pure isoniazid, isoniazid-sucrose, isoniazid-copper-sucrose, and isoniazid-copper-PEG-sucrose, all in equal molar ratios. The x-axis provides the various concentrations added to the broth culture (micromolar), while the y-axis measures the percent growth of the microbe.

Table four provides the MIC, $IC_{50}$, and $IC_{90}$ values of all four complexes under aerobic conditions. $IC_{50}$ and $IC_{90}$ values were determined from the drugs concentrations (x-axis, log values) plotted against the experimentally determined inhibition values. These values are the determination of the efficacy of a drug in inhibiting a biochemical cycle that impacts the ability of an organism to function. These values are often used for in vitro measurements while the $EC_{50}$ methods are used for in vivo measurements. Isoniazid had lower MIC (0.97 micromolar), $IC_{50}$ (0.63 micromolar), and $IC_{90}$ (1.0 micromolar) values than when complexed with sucrose and when complexed with both copper(II) and sucrose. However, the three component complex sucrose-PEG-copper-isoniazid had lower MIC (0.21 micromolar), $IC_{50}$ (0.16 micromolar), and $IC_{90}$ (0.21 micromolar) values compared to isoniazid alone. Combining the copper(II) ion with the isoniazid-sucrose complex increased the MIC and both IC values. This indicates that the three component complex deliver system can potentially have four additional medicinal benefits when compared to isoniazid alone. First, lower dosages of the antibiotic could be used when treating a tuberculosis infection. Second, if lower dosages are used to obtain the same level of pharmaceutical activity then the extent of the side effects, which can be significant with anti-tuberculosis drugs, could be lessened. Third, depending on dosage manipulation, a lower MIC value for a drug could indicate a shorter treatment length. Currently, treatment length for tuberculosis typically lasts six months. Fourth, the PEG-copper-isoniazid-sucrose aggregate may be perceived as biological waste to the human immune system and the macrophage may engulf it via the process of phagocytosis.

Table five provides the MIC, $IC_{50}$, and $IC_{90}$ values of all four complexes under low oxygen conditions using a low oxygen recovery assay (LORA). Isoniazid had the lowest MIC (0.62 micromolar) and $IC_{90}$ (0.46 micromolar) values compared to isoniazid complexed with copper, sucrose, and PEG. However, the copper-isoniazid-sucrose-PEG complex had a slightly lower $IC_{50}$ (0.3 micromolar) value compared to isoniazid alone (0.35 micromolar).

Table six provides the minimum bactericidal concentration (MBC), or the minimum concentration of an antibiotic that is needed to kill the bacteria, values which demonstrate that all four complexes tested were considered to be bactericidal. MBC values are measured by a broth dilution and subculturing to agent-free agar plates and are calculated by determining the lowest compound concentration needed to reduce the starting bacterial inoculation by greater than ninety-nine percent (99.9%). Antibacterial agents are considered bactericidal if the MBC/MIC value is less than four. Pure isoniazid exhibited the lowest MBC (0.3 micromolar) value compared to the other three complexes; while copper-isoniazid-sucrose and copper-isonaizid-sucrose-PEG had the same MBC value (1.4 micromolar). Adding the copper ion and PEG reduced the MBC value of isoniazid-sucrose by about half Table seven provides data that demonstrates two of the four complexes were considered cytotoxic towards eukaryotic cells and both contained sucrose: copper-isoniazid-sucrose ($IC_{50}$ 53 micromolar) and copper-isoniazid-sucrose-PEG ($IC_{50}$ 32 micromolar). Eukaryotic cells are characteristic of all life except bacteria, blue-green algae, and some primitive microbes, compared to a prokaryote cell which is characteristic to bacteria and other single-celled organisms. Cytotoxicity is the ability of a compound to be toxic to cells. Isoniazid exhibits cytotoxicity in vivo and results with clinical side effects. The lower MIC values for isoniazid against active tuberculosis (see table four) suggest that a lower dose could be possible which could lower the cytotoxicity. While PEG, copper(II), sucrose and isoniazid are not cytotoxic at these concentrations, the results of the combination indicate a chemical reaction or reactions that impact one or more cellular processes. The cytotoxic and MIC values indicate there is a concentration range lower than the cytotoxicity limit and above the MIC values allowing additional testing for dosage determination.

Table eight shows all four isoniazid based complexes had intracellular activity against *M. tuberculosis*. *M. tuberculosis* can survive in host macrophages for long periods of time (i.e. weeks). A published study entitled "Intracellular Activity of Tedizolid Phosphate and ACH-702 versus *Mycobacterium Tuberculosis* Infected Macrophages," demonstrated intracellular activity for two new compounds, Tedizolid and ACH-702 which resulted in a drop of activity of approximately 1.4 and 1.3 log(kill) units. As the data in table eight demonstrates, the average log(kill) value for isoniazid is 2.5. None of the three components of the drug carrier interfere with the medicinal activity of isoniazid in this process. A drug with intracellular activity can impact pharmacokinetic parameters such as penetration and retention, accumulation, subcellular disposition, bioavailability and metabolism. The drug can also impact pharmacodynamic parameters such as expression of activity and bacterial responsiveness. While PEG, copper, sucrose and isoniazid are not independently cytotoxic at these concentrations, the results of the combination indicate a chemical reaction or reactions that impact one or more cellular processes. The catalase-peroxidase enzyme in *M. tuberculosis* katG is responsible for activation of the drug. KatG causes isonicotinic acyl-NADH to form, which inhibits the production of different forms of mycolic acids, a major component of the cell wall of *M. tuberculosis*. Isoniazid is bactericidal to mycobacteria that reproduce rapidly, but it is bacteriostatic if the bacteria are slow-growing.

Table nine provides data that illustrates four of the eight complexes exhibited increased efficacy to isoniazid resistant isolates (INH-R1, INH-R2). The history and concepts of bacterial resistance is critical in recognizing the significance of these results. Bacterial resistance occurs when an isolate evolves a mutation to avoid the mechanism of action of an antibiotic. These bacteria then replicate and cause an infection that cannot be affected by the antibiotic to which the isolate has developed a resistance to.

The isoniazid resistant isolates tested were derived from the H37Rv strain and contained a mutation in the katG gene. The copper-isoniazid-sucrose-PEG complex clearly exhibited the lowest MIC values compared to the other four compounds at 25 and 28 micromolar, followed by the copper-isoniazid-sucrose complex at 89 and 92 micromolar. The isoniazid and isoniazid-sucrose complexes exhibited higher MIC values at >200 micromolar. The isolates showed the highest resistance to isoniazid and isoniazid-sucrose and the lowest resistance to the complex containing all four compounds: copper, sucrose, PEG, and isoniazid. Pure isoniazid and the isoniazid-sucrose complexes had measured MIC values that were greater than two hundred micromolar, values that would be toxic if administered at these high concentrations. Considering the total compilation of measurements (tables four, five, six, seven, eight, nine), the three component aggregate has unique medicinal features of being toxic against *M. tuberculosis* and having the ability to kill its host. As the controls in various studies demonstrate, none of the individual components have these properties but the sum total of the three combined with the antibiotic possess these pharmaceutical traits. In presenting a novel aspect of this work, there is no record in the scientific literature of repurposing a known first or second-line antibiotic making it active again against a bacterium that has developed a resistance mechanism to it using an altered molecular delivery system.

Another series of experiments involving *M. tuberculosis* cell line measurements that replaced the disaccharide sucrose molecule with the monosaccharide glucose molecule were performed. A total of four complex combinations, including the frontline antibiotic isoniazid, the monosaccharide glucose, the copper(II) ion, and PEG-3350 were tested against the *M. tuberculosis* H37Rv strain at the National Institutes of Health—National Institute of Allergy and Infectious Disease (NIH-NIAID). These complexes contained different ratios of glucose and PEG, and the MIC and IC values were found in aerobic conditions.

Table ten provides the MIC, $IC_{50}$, and $IC_{90}$ values of the five complex variations. Each complex exhibited activity against the bacterium under aerobic conditions. Isoniazid had the lowest MIC (0.64 micromolar), $IC_{50}$ (0.47 micromolar), and $IC_{90}$ (0.62 micromolar) values compared to the complexes that contained glucose, copper, and PEG. When the ratios of glucose increased by four and sixteen fold in the complexes, the MIC, $IC_{50}$, and $IC_{90}$ values increased, indicating decreased pharmaceutical efficacy or that glucose inhibited isoniazid. When the quantity and concentration of PEG was increased by four fold in the complexes, the MIC, $IC_{50}$, and $IC_{90}$ values increased, also demonstrating that PEG lessened the pharmaceutical efficacy of isoniazid in the presence of glucose.

The scientific hypothesis related to the development of this embodiment outlines four unique features related to the tablet composition and how its effectiveness compares to existing drug delivery systems in vivo and in vitro; (a) sucrose and copper would serve as biocides and/or toxic species or aid in enhancing these activities of the antibiotic (b) a water soluble polymer would produce an aggregate that could assimilate and enclose the components and antibiotic and this aggregate would be identified as foreign by the macrophage and be consumed, providing an entry method to the protected M. tuberculosis (c) copper and sucrose would serve as nutrient based components, would be delivered with the antibiotic in the PEG aggregate because they are similar in size to the drug, and serve a role in potentially accelerating some cellular processes, (d) the water soluble polymer forms a loosely shaped aggregate that could increase residence time in the patient and minimize hydrogen bonding to the drug and unwanted species.

The tablet composition and the pharmaceutical results of this composition are significant for two reasons. One is that it is the first known demonstration of an existing front-line antibiotic exhibiting a reversal of resistance making the highly utilized antibiotic effective again against resistant strains of M. tuberculosis. Since many aspects of the front-line antibiotics, such as isoniazid, are already known, this development allows for the same medicinal agents to continue being used, rather than developing a new compound with anti-tuberculosis properties. This technology provides not only a medical advantage but also an economic one, since these drugs are already manufactured, distributed and stored worldwide. Second, this technology is the first positive demonstration of a nutrient based drug delivery system focused on being masked from the immune system and altering cellular processes with anti-tuberculosis properties.

TABLE 4

All four complexes had activity against M. tuberculosis under aerobic conditions.

| Complexes | MIC (μM) | IC$_{90}$ (μM) | IC$_{50}$ (μM) |
|---|---|---|---|
| Isoniazid (INH) | 0.97 | 1.0 | 0.63 |
| INH-SUC | 1.3 | 1.3 | 0.71 |
| Cu-INH-SUC | 2.3 | 2.7 | 1.6 |
| Cu-INH-SUC-PEG | 0.21 | 0.21 | 0.16 |

TABLE 5

All four complexes had activity against M. Tuberculosis under low oxygen concentrations.

| Complexes | Low Oxygen MIC (μM) | Low Oxygen IC$_{50}$ (μM) | Low Oxygen IC$_{90}$ (μM) |
|---|---|---|---|
| Isoniazid (INH) | 0.62 | 0.35 | 0.46 |
| INH-SUC | 3.7 | 2.0 | 2.7 |
| Cu-INH-SUC | 41 | 1.1 | 6.3 |
| Cu-INH-SUC-PEG | 69 | 0.3 | 4.2 |

TABLE 6

Figure 1:
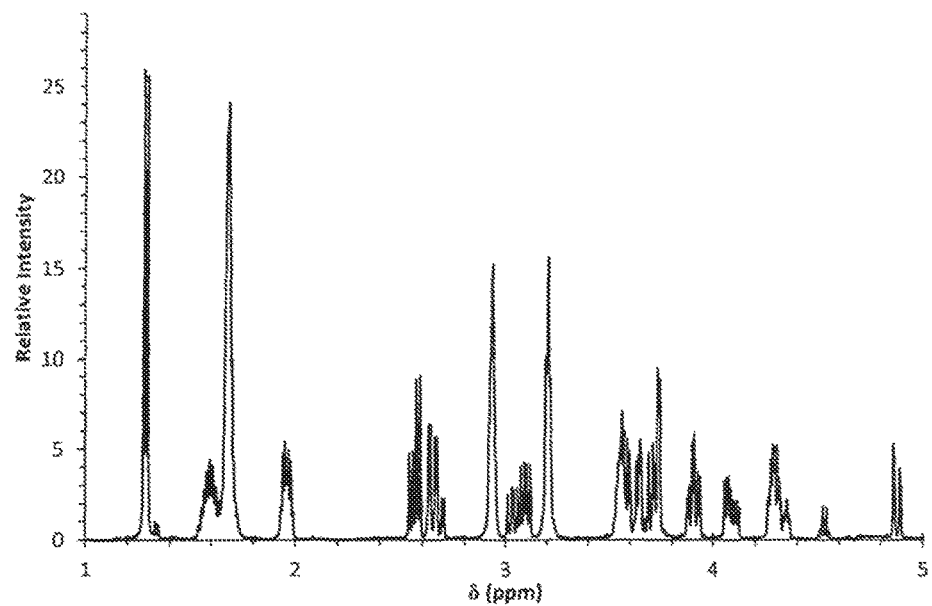
FIG. 1: (A, top) 500 MHz $^1$H NMR spectra of the second line TB drug capreomycin and the (B, bottom) copper-capreomycin complex. The paramagnetic copper ion causes shifts and broadening to the entire NMR structure indicating the ion is moving around the structure and not bound to a single location when in the solvent.
Figure 1:
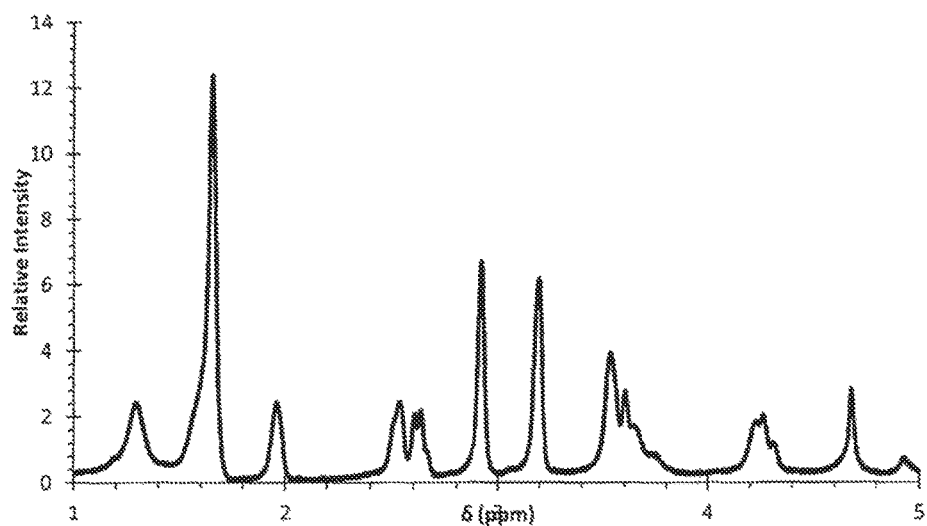
Figure 2:
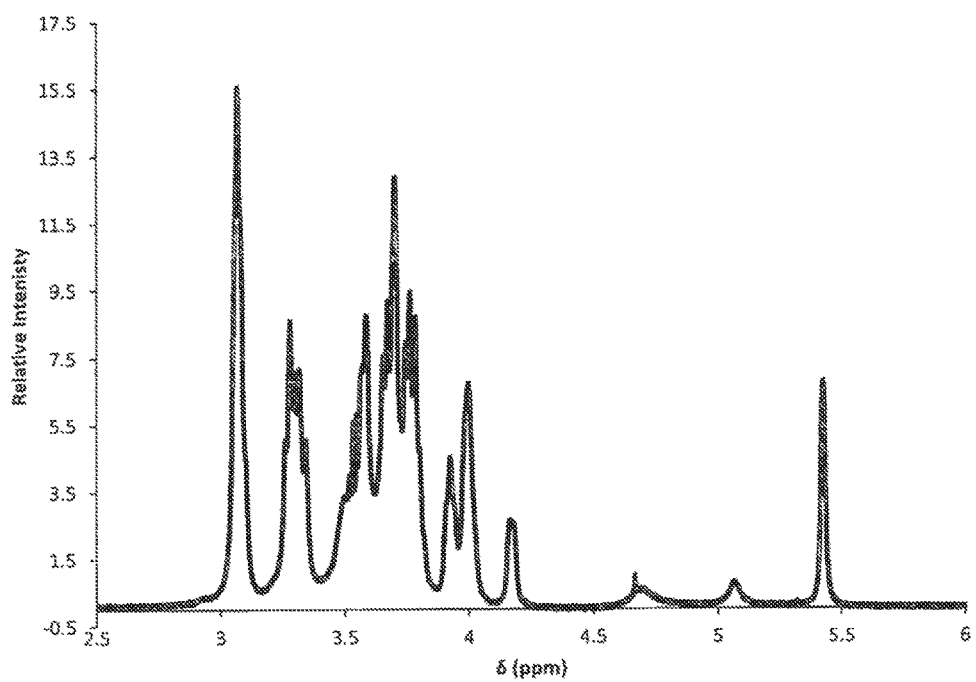
FIG. 2. A 500 MHz proton ($^1$H) NMR spectra of the copper-amikacin complex between 2.5 and 6 ppm. The broadened spectral features indicate the paramagnetic copper dication is interacting with the entire molecule.
Figure 3:
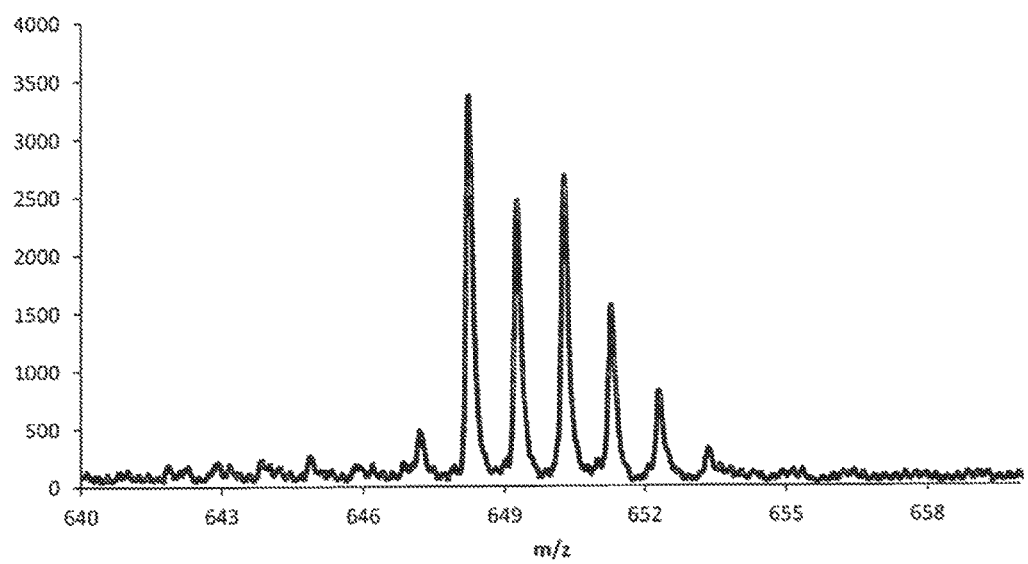
FIG. 3. A MALDI-TOF-MS spectrum of the copper-amikacin complex. The isotopic peaks and their natural abundance for the complex are 648.2 m/z (51.6%), 649.2 (13.1%), 650.2 (26.1%), 651.2 (6.6%) and 652.2 (1.47%). This is experimental evidence that the copper ion is bound to the antibiotic.
Figure 4:
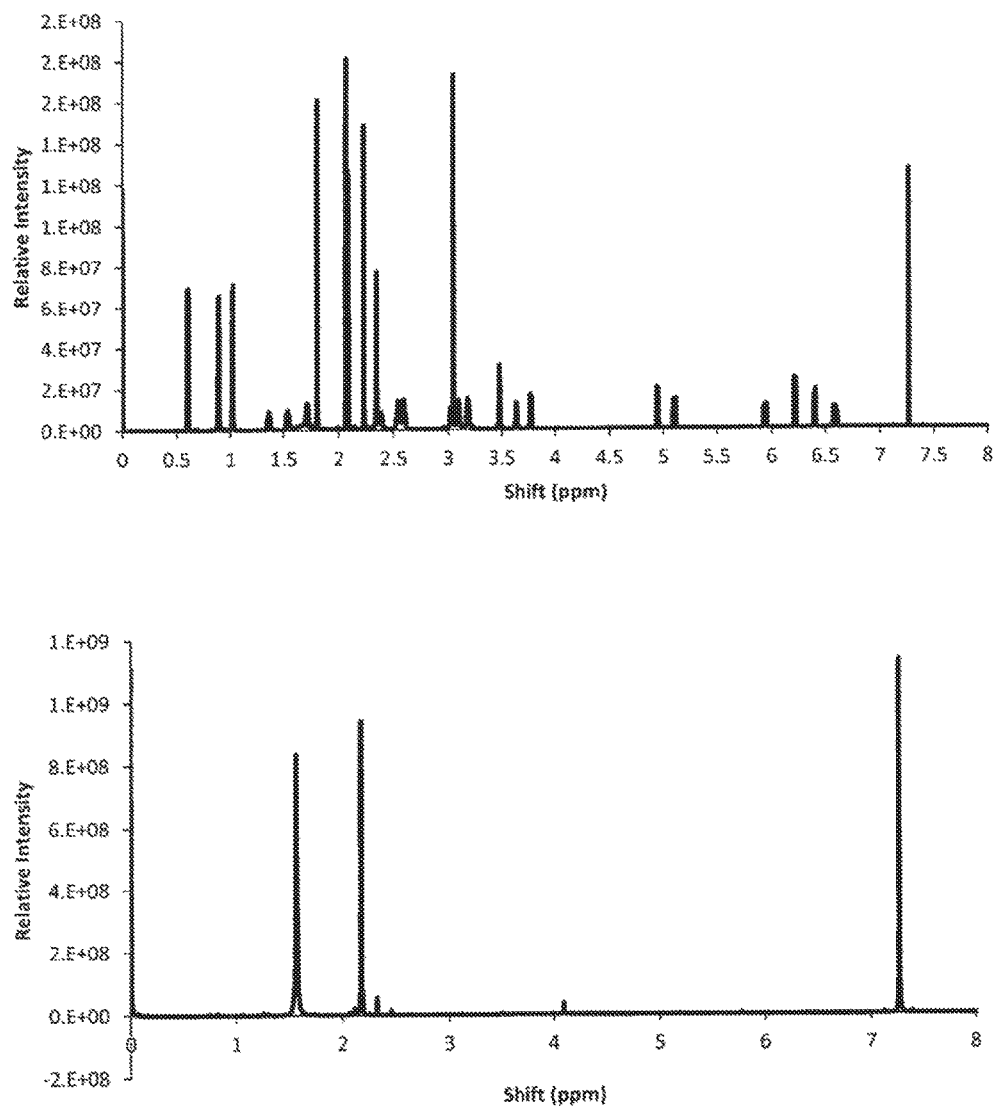
FIG. 4. A proton ($^1$H) NMR spectra of rifampicin (top) and of the copper-rifampicin complex (bottom). The paramagnetic copper ion can cause a spectral feature in NMR to be so broadened so it raises the baseline and is not observed by the analyst.
Figures 5A, 5B:
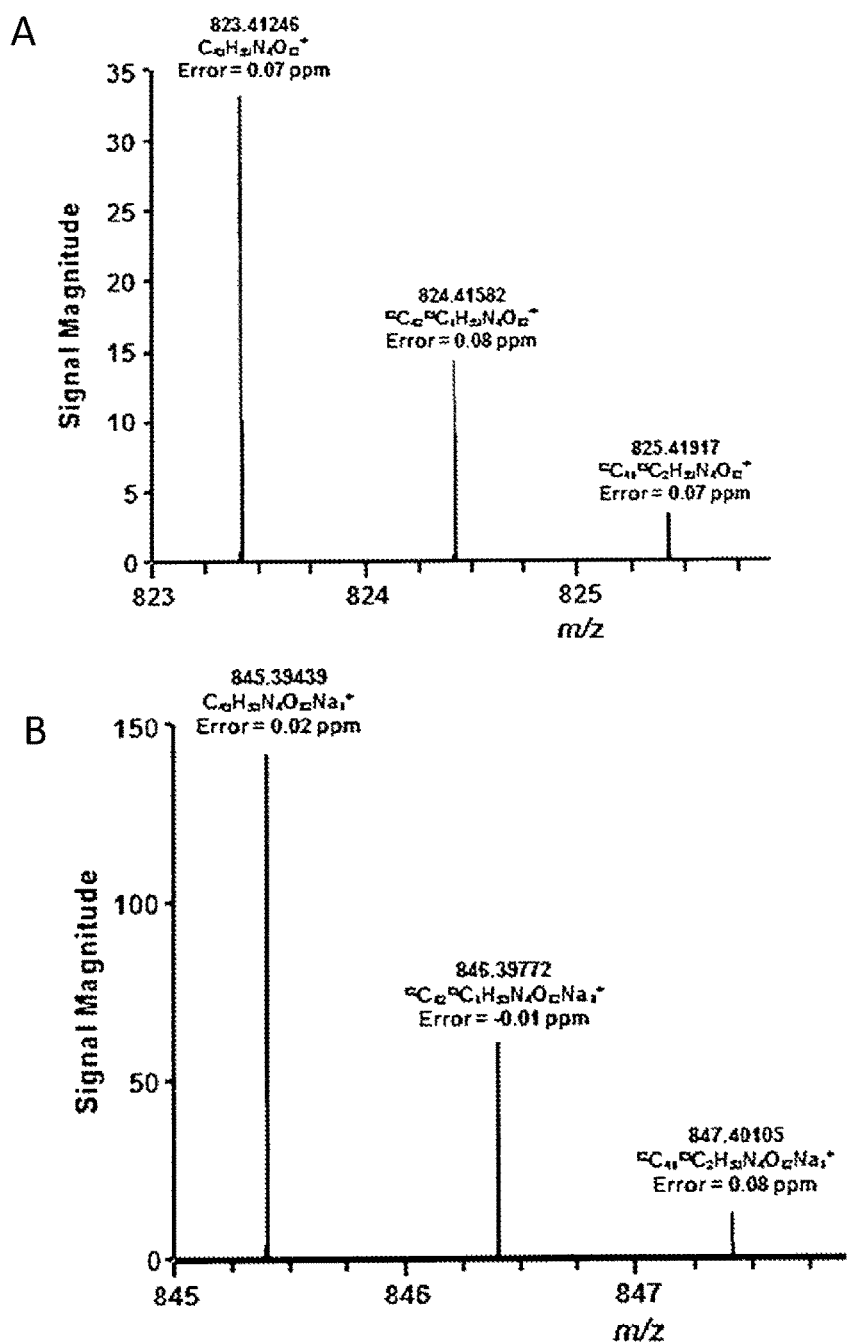
FIG. 5 (A-D). FT-ICR provides the best resolution and mass accuracy available for molecular analysis. (A) Provides spectral data for rifampicin $C_{43}H_{58}N_4O_{12}$—H$^+$ (B) Provides spectral data for the presence of the ubiquitous sodium adduct of rifampicin (C) Provides spectral evidence for the presence of the copper-rifampicin complex minus water (D) Provides spectral evidence for the presence of the copper-rifampicin complex.
Figures 5C, 5D:
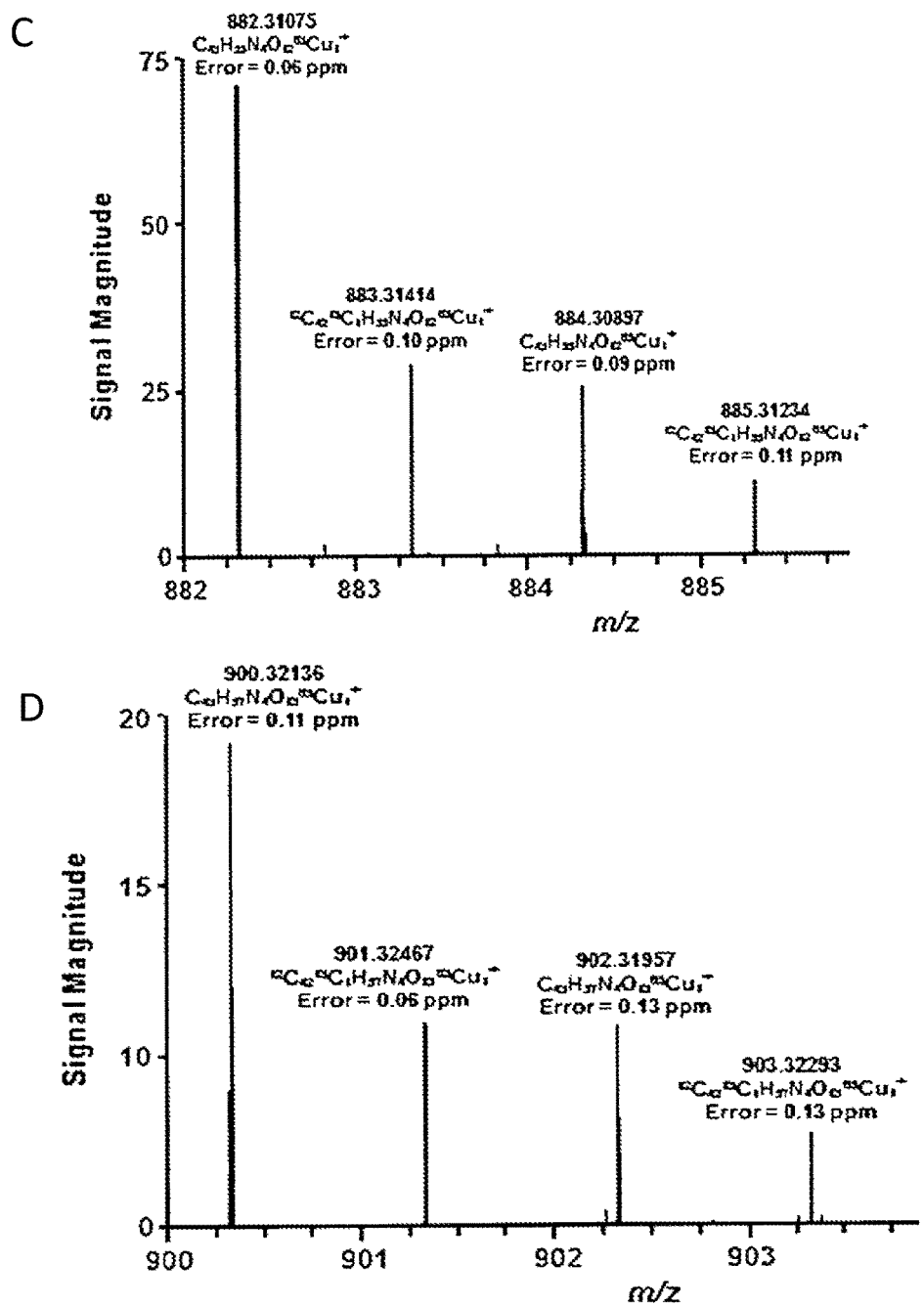
Figure 6A:
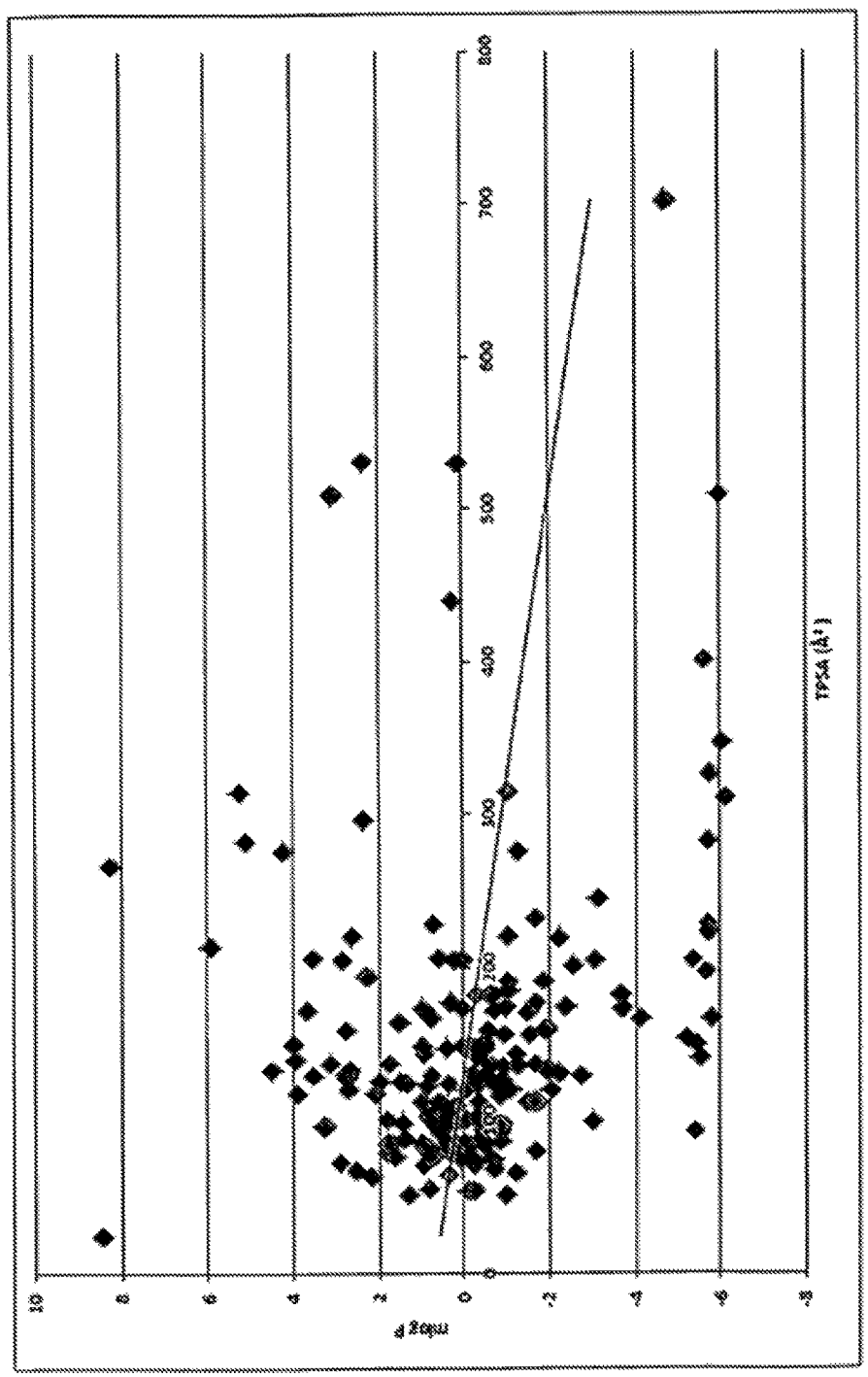
FIGS. 6A and 6B are logP graphs of 187 antibiotic complexes. (A) The logP (i.e. the log$_{10}$) value of the water-octanol partition coefficient is plotted against the number of hydrogen bond donors for 187 antibiotic complexes (B) the logP is plotted against the total polar surface area (TPSA) for 187 antibiotic complexes.
Figure 6B:
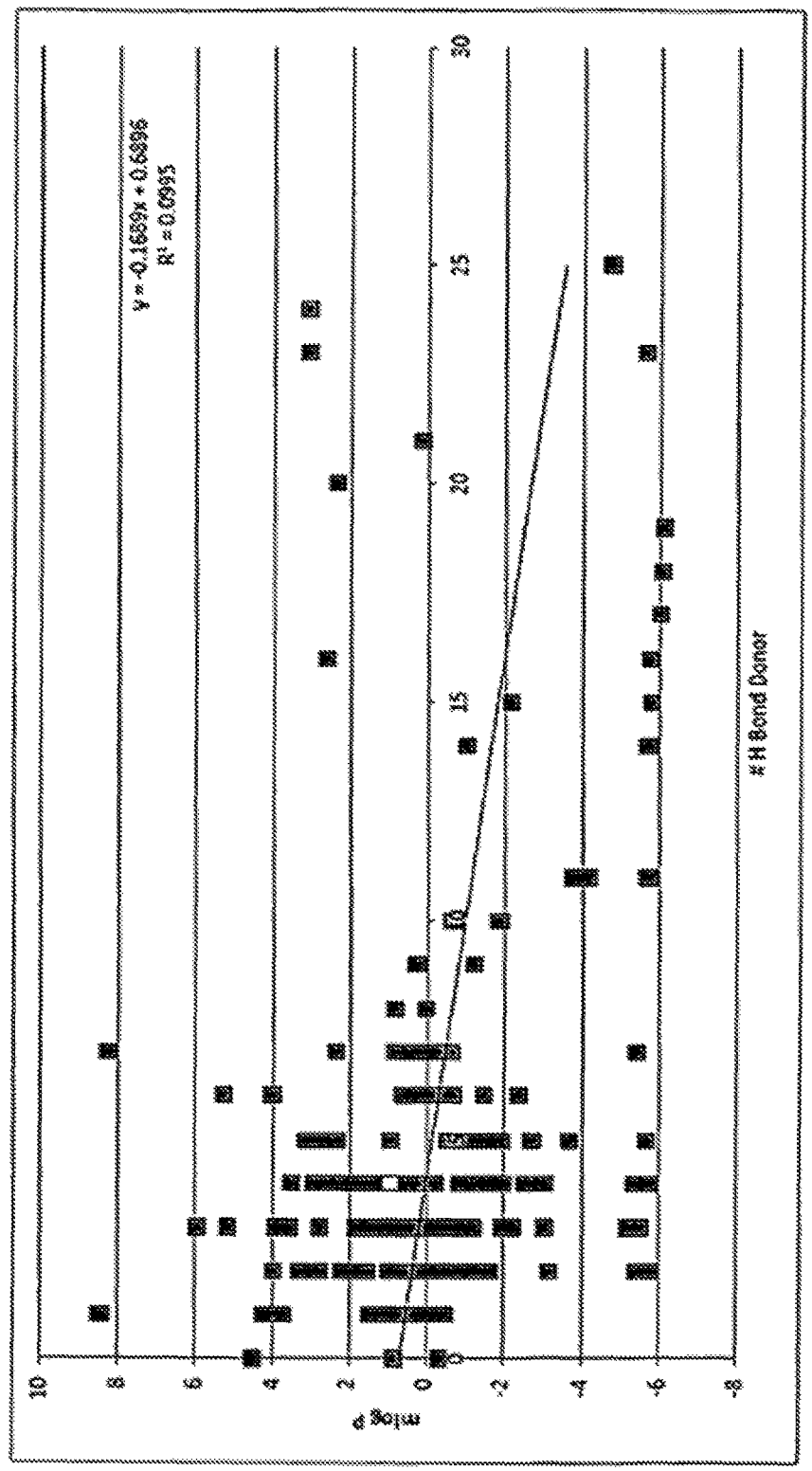
Figure 7:
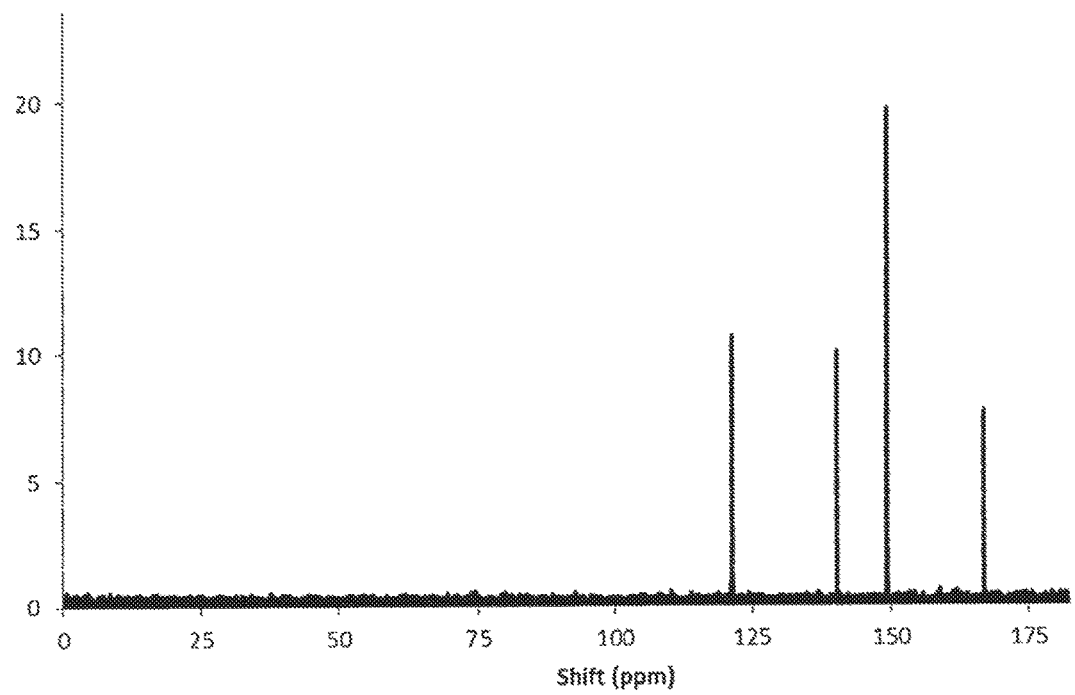
FIG. 7. The 500 MHz $^{13}$C NMR of isoniazid shows the four spectral features corresponding to the four carbons species.
Figure 8:
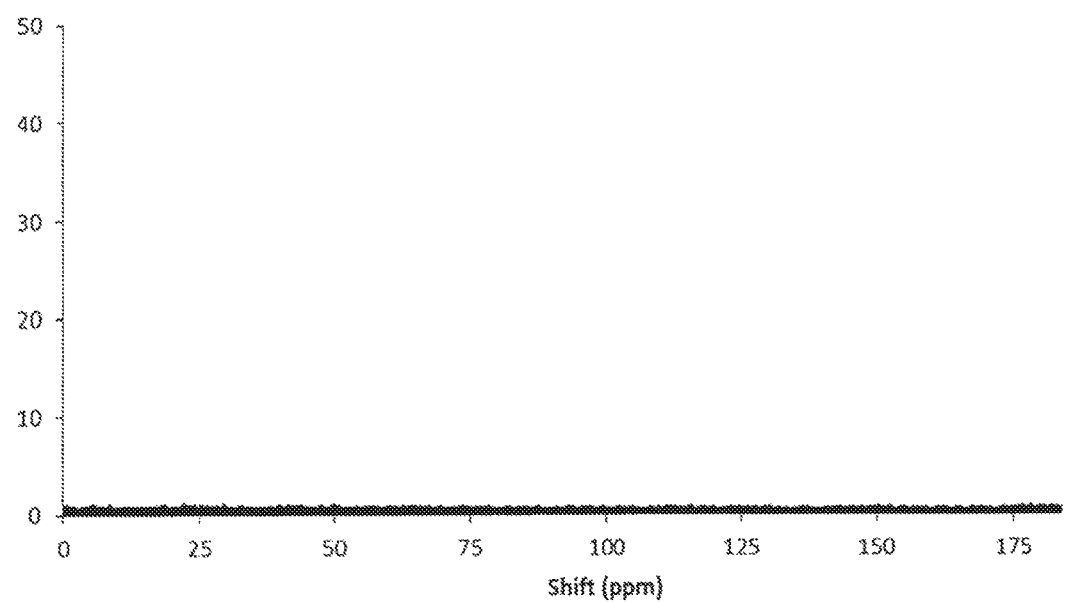
FIG. 8. The $^{13}$C NMR of the copper(II)-isoniazid complex illustrates how the paramagnetic copper causes the spectral features to disappear.
Figure 9:
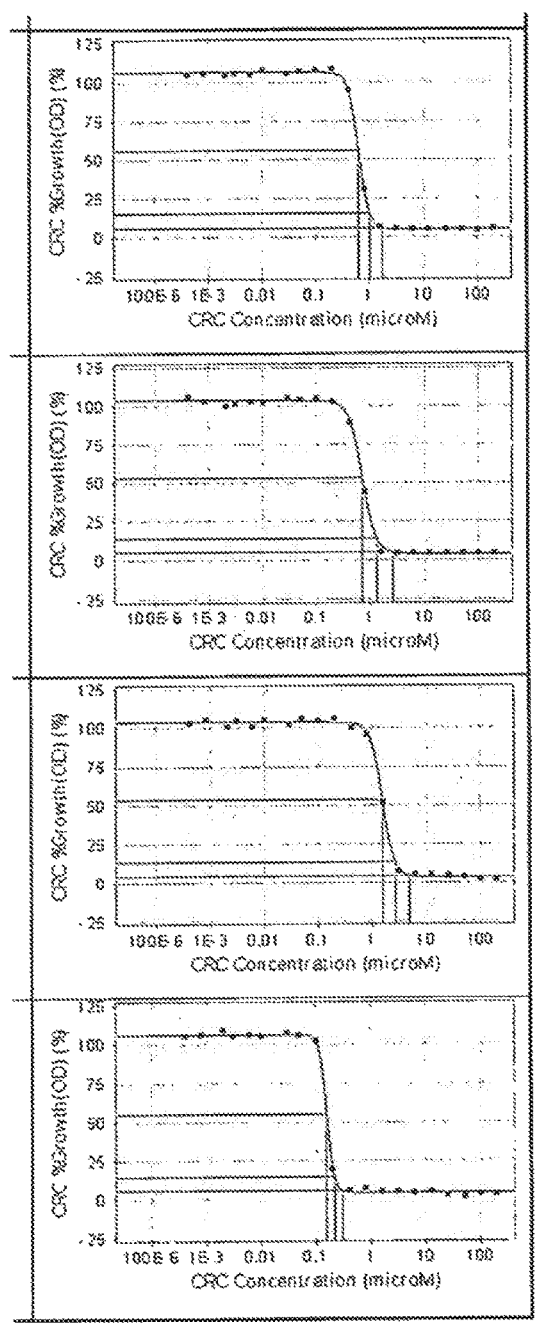
FIG. 9. Dose response curves for (from top) isoniazid, isoniazid-sucrose, isoniazid-sucrose-copper; and isoniazid-sucrose-copper-PEG, all in equal molar ratios. Dose response curves were used to calculate the MIC, IC$_{50}$ and IC$_{90}$ values.

All four complexes had bactericidal properties.

| Compound | MBC (μM) |
|---|---|
| Isoniazid (INH) | 0.3 |
| INH-SUC | 3.1 |
| Cu-INH-SUC | 1.4 |
| Cu-INH-SUC-PEG | 1.4 |

TABLE 7

Two complexes have cytotoxic effects against eukaryotic cells. This data suggest that the compound(s) can affect the macrophages that harbor M. tuberculosis.

| Compound | IC$_{50}$ (μM) |
|---|---|
| INH | >100 |
| INH-SUC | >100 |
| Cu-INH-SUC | 53 |
| Cu-INH-SUC-PEG | 32 |

TABLE 8

Four complexes had intracellular activity against *M. tuberculosis*.

| Complexes | Concentration (μM) | Log Kill |
|---|---|---|
| Isoniazid (INH) | 1.2 | 2.5 |
| Isoniazid (INH) | 12 | 2.5 |
| INH-SUC | 0.62 | 2.2 |
| INH-SUC | 6.2 | 2.7 |
| Cu-INH-SUC | 14 | 2.7 |
| Cu-INH-SUC-PEG | 1.4 | 2.4 |
| Cu-INH-SUC-PEG | 14 | 2.5 |

TABLE 9

*M. tuberculosis* isoniazid resistant isolates showed increased resistance to four of eight complexes.

| Complexes | MIC (μM) | Resistant Isolate |
|---|---|---|
| Isoniazid (INH) | >200 | INH-R1 |
| Isoniazid (INH) | >200 | INH-R2 |
| INH-SUC | >200 | INH-R1 |
| INH-SUC | >200 | INH-R2 |
| Cu-INH-SUC | 89.0 | INH-R1 |
| Cu-INH-SUC | 92.0 | INH-R2 |
| Cu-INH-SUC-PEG | 25 | INH-R1 |
| Cu-INH-SUC-PEG | 28 | INH-R2 |

TABLE 10

All five complexes, including four that incorporated glucose, had activity against *M. tuberculosis* under aerobic conditions.

| Complexes | MIC (μM) | $IC_{50}$ (μM) | $IC_{90}$ (μM) |
|---|---|---|---|
| Isoniazid (INH) | 0.64 | 0.47 | 0.62 |
| Cu-INH-GLU-PEG | 2.7 | 1.7 | 2.5 |
| Cu-INH-$GLU_4$-PEG | 1.8 | 1.1 | 1.8 |
| Cu-INH-$GLU_{16}$-PEG | 12 | 8.8 | 11 |
| Cu-INH-GLU-$PEG_4$ | 4.2 | 2.8 | 4.7 |

What is claimed is:

1. A pharmaceutical composition comprising i. one or more front line antibiotics used in the treatment of the bacterial infection *Mycobacterium tuberculosis;* ii. sucrose, wherein its mass percent is a minimum of about one percent and a maximum of fifty percent of the total composition mass;

iii. copper (Cu), which is present in an amount from at least about one percent to about forty percent of the total mass of the composition; and iv. a polyethylene glycol (PEG) polymer wherein its mass percent is a minimum of at least five percent and a maximum of 90% of the total composition mass.

2. The pharmaceutical composition according to claim 1, wherein the antibiotic is an anti-tuberculosis antibiotic selected from the group consisting of ethambutol (EMB), isoniazid (INH), pyrazinamide (PZA), rifampicin (RIF), rifabutin (RBT), and rifapentine (RPT).

3. The pharmaceutical composition according to claim 1, wherein the copper is copper (I) or copper (II).

4. The pharmaceutical composition according to claim 1, wherein the copper is a combination of copper (I) and copper (II).

5. The pharmaceutical composition according to claim 1, wherein the polyethylene glycol comprises the repeating unit $(C_2H_40)_n$ where n is between ten and two hundred.

6. The pharmaceutical composition according to claim 1, wherein the composition is compounded using wet granulation procedures or dry granulation procedures; and is dried using a tray-dryer or a fluid-bed dryer.

7. The pharmaceutical composition according to claim 1, wherein the composition has a mass less than two thousand milligrams.

8. A method of formulating the composition of claim 1 comprising binding the transition metal cation with the saccharide to form a metal ligand complex and combining the metal ligand complex with at least polyethylene glycol and one or more front line antibiotics.

9. A method of formulating the composition of claim 1 comprising mixing the front line antibiotic with polyethylene glycol, binding the transition metal cation with the saccharide to form a metal ligand complex, and then combining the metal ligand complex with the mixed front line antibiotic and polyethylene glycol.

10. The composition of claim 1, further comprising pharmaceutically acceptable binders; disintegrants; glidants; solvents; lubricants; coatings; and/or other excipients that have a total percent of at least five percent of the total composition mass.

11. The composition of claim 1, wherein the PEG is PEG-3350.

12. The pharmaceutical composition of claim 1, wherein the one or more front line antibiotics, sucrose, copper, and PEG polymer are in a molar ratio of 1:1:1:1.

13. The pharmaceutical composition according to claim 11, wherein the composition dissolves in water and forms aggregates; wherein the aggregates can enclose and transport the antibiotic in vivo.

* * * * *